(12) United States Patent
Jusoh et al.

(10) Patent No.: US 6,207,946 B1
(45) Date of Patent: Mar. 27, 2001

(54) ADAPTIVE LIGHTING SYSTEM AND METHOD FOR MACHINE VISION APPARATUS

(75) Inventors: Noor Ashedah Binti Jusoh; Tan Seow Hoon; Sreenivas Rao, all of Singapore (SG)

(73) Assignee: Semiconductor Technologies & Instruments, Inc., Plano, TX (US)

( * ) Notice: Subject to any disclaimer, the term of this patent is extended or adjusted under 35 U.S.C. 154(b) by 0 days.

(21) Appl. No.: 09/360,656

(22) Filed: Jul. 26, 1999

Related U.S. Application Data

(63) Continuation-in-part of application No. 09/146,565, filed on Sep. 3, 1998, now abandoned.

(51) Int. Cl.[7] .............................. G01N 21/84; H04N 7/18
(52) U.S. Cl. ................. 250/208.1; 250/553; 250/559.34; 250/559.46; 348/87; 348/126; 348/131
(58) Field of Search ................................... 250/205, 552, 250/553, 559.04, 559.07, 559.08, 559.16, 559.34, 559.39, 559.45, 559.46, 227.11, 227.2; 356/240.1, 237.4, 237.5, 394; 348/86, 87, 92, 125, 126, 131; 382/141, 145, 147; 315/159, 158; 385/116

(56) References Cited

U.S. PATENT DOCUMENTS

| | | |
|---|---|---|
| 4,882,498 * | 11/1989 | Cochran et al. ............... 250/559.04 |
| 5,172,005 | 12/1992 | Cochran et al. . |
| 5,365,084 | 11/1994 | Cochran et al. . |
| 5,621,218 | 4/1997 | Tanaka . |
| 5,870,203 | 2/1999 | Chiu et al. . |

* cited by examiner

Primary Examiner—John R. Lee
(74) Attorney, Agent, or Firm—Akin, Gump, Strauss, Hauer & Feld, L.L.P.

(57) ABSTRACT

A variable intensity lighting system for use with a machine vision apparatus for capturing high contrast images of articles to be inspected, such as semiconductor packages, includes an LED or optical fiber element and flash lamp array configured in multiple segments which are operable to be controlled as to light output intensity by a programmable intensity control circuit operably connected to a microprocessor. The intensity control circuit includes multiple digital potentiometers operable to control selected segments of the lighting array. The control circuit is adapted to control up to 64 segments of the lighting array individually at 64 incremental intensity levels, respectively. The control circuit may include a light failure module to detect a segment failure or a reversed connection. A processor is programmed to calculate a median gray value from a predetermined number of camera pixel intensity values of the article being viewed under the lighting array to readjust the intensity of the lighting until a setting with suitable contrast is reached. Each article being viewed may have a suitable identifier, such as a dimple or notch which is viewed by the camera to determine the optimum intensity level.

28 Claims, 19 Drawing Sheets

| INPUTS | | | | OUTPUTS | | | |
|---|---|---|---|---|---|---|---|
| SELECT BIT 0 | SELECT BIT 1 | SDA1/ SCL1 | SDA2/ SCL2 | SDA1 | SCL1 | SDA2 | SCL2 |
| 0 | 0 | 0 | 0 | 0 | X | 0 | X |
| 0 | 0 | 1 | 0 | 1 | X | 0 | X |
| 0 | 1 | 0 | 0 | X | 0 | X | 0 |
| 0 | 1 | 1 | 0 | X | 1 | X | 0 |
| 0 | 0 | 0 | 0 | X | X | 0 | X |
| 0 | 0 | 0 | 1 | X | X | 1 | X |
| 0 | 1 | 0 | 0 | X | X | X | 0 |
| 0 | 1 | 0 | 1 | X | X | X | 1 |

FIG. 9

| DEVICE | ADDRESS (A3.A2.A1.A0) | DEVICE | ADDRESS (A3.A2.A1.A0) |
|---|---|---|---|
| U17 | 0000 | U26 | 1001 |
| U18 | 0001 | U27 | 1010 |
| U19 | 0010 | U28 | 1011 |
| U20 | 0011 | U29 | 1100 |
| U21 | 0100 | U30 | 1101 |
| U22 | 0101 | U31 | 1110 |
| U23 | 0110 | U32 | 1111 |
| U24 | 0111 | U33 | 0000 |
| U25 | 1000 | | |

FIG. 10

ADAPTIVE LIGHTING SYSTEM AND METHOD FOR MACHINE VISION APPARATUS

CROSS REFERENCE TO RELATED APPLICATION

This Application is a continuation-in-part of U.S. patent application Ser. No. 09/146,565, filed: Sept. 3, 1998, now abandoned.

FIELD OF THE INVENTION

The present invention pertains to a lighting system for use with a machine vision apparatus, such as used in the inspection of semiconductor packages, wherein the lighting system automatically adapts to the particular object being inspected to provide an improved image of the object viewed by the vision apparatus to improve the accuracy of an inspection process or to carry out other processes.

BACKGROUND

In the manufacture of semiconductor or microelectronic circuits or so-called packages, several processes may be carried out by machine vision systems, including inspection of the package electrical leads to determine if any leads are out of place or damaged, or inspection of the package for certain markings placed thereon. Machine vision systems have been developed to carry out these tasks in view of the need to automate the manufacturing process for semiconductor packages, taking into consideration the substantial number of such packages which are produced. Moreover, many inspection and marking systems for processing semiconductor packages are adapted to handle various configurations of packages having different shapes, lead configurations and light reflecting characteristics.

In this last mentioned regard, a lighting system which is set up for the proper contrast or image for one type of package usually requires adjustment for a different type of package. Still further, packages of essentially the same type or configuration may be fabricated of different materials which have at least slightly different light reflectivity characteristics. Therefore, a vision apparatus adapted for inspecting a particular type of semiconductor package may not function properly if slight changes in materials used for the packages or any changes in the light reflectivity of the package occurs which will change the contrast and the quality of the image captured by the inspection or vision apparatus.

Accordingly, there has been a need for a lighting system for machine vision apparatus which is adaptable to vary the light intensity on various parts of an article or device being inspected, such as various types of integrated circuit or semiconductor packages, to enhance the image of the package, as viewed by a vision apparatus. Moreover, there has also been a need for a system which will automatically adjust the lighting imposed on different types of articles being inspected or otherwise viewed by a vision apparatus to enhance the accuracy of an inspection process or any process which requires machine vision of an article, such as an electronic circuit or semiconductor package. Still further, since the intensity and pattern of the lighting imposed on different articles being inspected is important, it is also important to provide for monitoring the failure of any part of the lighting system so that improper lighting and inspection of articles being illuminated by the system is not experienced. It is to accomplish the desiderata mentioned above and overcome problems associated with prior art apparatus that the present invention has been developed.

SUMMARY OF THE INVENTION

The present invention provides an improved lighting system for use with machine vision apparatus for inspecting or otherwise processing various types of articles including, in particular, electronic semiconductor devices or packages and the like.

In accordance with one important aspect of the present invention a lighting system is provided which is adapted to provide a predetermined contrast or image quality of an article being viewed by a machine vision apparatus so that an accurate image of the article being viewed is produced. One embodiment of the adaptive lighting system is preferably provided with an array of light emitting diodes (LEDs), which are arranged in multiple geometric segments so that a plurality of LEDs in one segment of the array may emit light of a certain intensity while the light emitting elements (LEDs) of other segments are adjusted to emit light of other intensities to optimize the image of an article being inspected, which image may be captured by a machine vision apparatus.

In accordance with another aspect of the present invention, an adaptive lighting system is provided which includes a programmable lighting array intensity control circuit which is operable to control a substantial number of segments of an LED lighting array, in particular. Moreover, the control circuit is operable in conjunction with a microprocessor which is operated with a program which performs lighting segment selection, intensity control for each segment energized and image intensity feedback.

In particular, the programmable intensity control circuit includes a plurality of digitally controlled potentiometers, all arranged on a monolithic CMOS microcircuit. The complete intensity control circuit, when interfaced with a digital input/output circuit connected to a microprocessor, will allow a vision apparatus to provide automatic adjustment of the light intensity on an article being illuminated and the provision of a substantial number of light intensity settings. The circuit is also adapted to include a constant current source for each lighting array segment and a single driver for both strobe and non-strobe illumination operations.

In accordance with still another aspect of the present invention, an adaptive lighting system is provided which includes a circuit for real time monitoring of light failure and providing a signal indicating at least one of the light segments of the lighting system has experienced a failure. The light failure monitoring circuit is included in a module provided for monitoring a failure of any of the lighting segments of the array or system and which includes an LED indicator for each light segment to indicate which segment has experienced a failure. The light failure monitoring circuit detects a discontinuity in or an open lighting circuit, reverse connections and LED failures resulting in either an open circuit or a short circuit.

In accordance with another aspect of the present invention, a lighting system is provided for use with machine vision apparatus which utilizes flash lamps and an array of fiber optic elements forming multiple light segments which may be used in place of or in addition to LED type lighting arrays to further increase the intensity of lighting for use in applications wherein the imaging system is required to capture an image of a moving object at very high "shutter" speeds. A lighting array including multiple bundles of fiber optic elements is coupled with an array of high intensity flash lamps providing the light source. A flash lamp driver/ trigger circuit is operably coupled to the programmable light intensity controllers through DC to AC inverters. The flash lamps may be energized by a continuous high frequency signal or by a single pulse type signal to provide multiple modes of operation.

The invention also provides a method for adjusting the intensity of a lighting array for lighting semiconductor packages and the like, which may be carried out by computing the median gray value of an image of an article or object, readjusting the lighting intensity and recomputing the median gray value until an optimum setting is reached.

The adaptive lighting system of the present invention eliminates the need for microprocessor based digital to analog converter circuits of types commercially available at the time of development of the invention and which types have been sufficient to provide for only a very limited number of segments of a lighting array to be controlled.

Those skilled in the art will further appreciate the advantages and superior features of the invention together with other important aspects thereof on reading the detailed description which follows in conjunction with the drawing.

BRIEF DESCRIPTION OF THE DRAWING

FIG. 9 is a logic table;

FIG. 10 is an address assignment table for components of the circuit shown in FIGS. 6A through 6G;

DETAILED DESCRIPTION OF PREFERRED EMBODIMENTS

Figure 1:
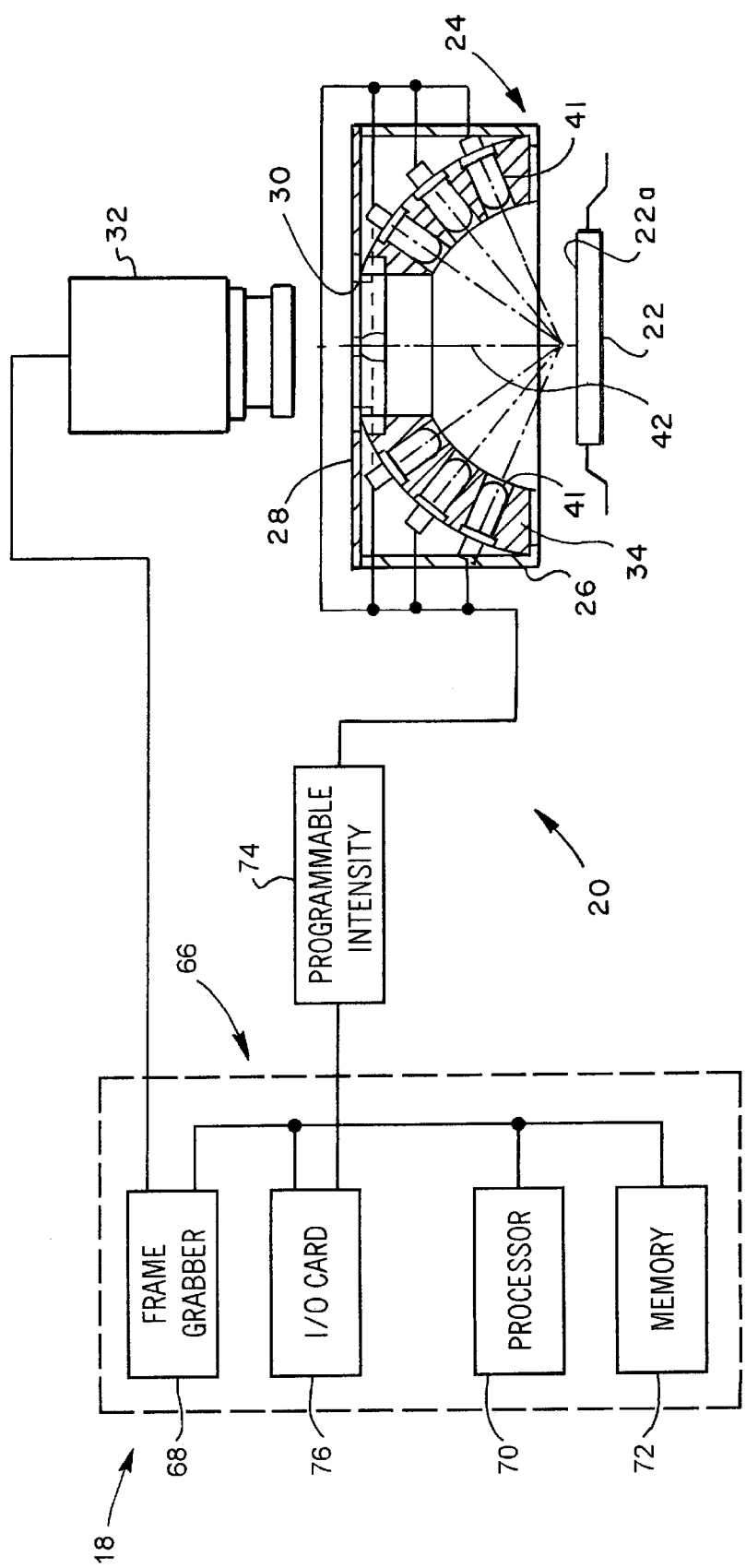
FIG. 1 is a schematic diagram of a machine vision apparatus including an adaptive lighting system in accordance with the invention.

In the description which follows like parts are marked throughout the specification and drawing with the same reference numerals, respectively. The drawing figures may not be to scale and certain components may be shown in generalized or schematic form and identified by commercial designations in the interest of clarity and conciseness.

Referring to FIG. 1, there is illustrated a generalized schematic diagram of a portion of a machine vision apparatus 18, including an adaptive lighting system 20, in accordance with the present invention. The lighting system 20 is adapted to be used in conjunction with machine vision apparatus 18, which may be one of the general types described in U.S. patent applications Ser. Nos. 08/890,814 and 09/069,056 filed on Jul. 11, 1997 and Apr. 28, 1998, respectively, and assigned to the assignee of the present invention, now U.S. Pat. Nos. 6,118,540 and 5,956,134. The adaptive lighting system 20 is not limited to use with the apparatus disclosed in the above-identified patent applications and the lighting system may be operated to illuminate various devices. However, the system 20 is particularly adapted for illuminating electronic circuit or semiconductor devices or "packages", such as the package 22 shown in FIG. 1. The package 22 may be one of many types known to those skilled in the art of machine vision apparatus used in semiconductor device manufacturing.

The package 22 may be disposed on a table, a transport belt or in a tray or other mechanism, all not shown, for moving the package 22 relative to the lighting system 20 into range to be illuminated by a lighting array 24. The lighting array 24 includes a suitable support housing 26 in the form of a generally rectangular boxlike shell, having a top wall 28 with a central, generally cylindrical aperture 30 formed therein, for viewing the package 22 by a suitable camera 32. The camera 32 may be of a type commonly used in machine vision systems including a charge coupled device (CCD) type camera.

Figure 2:
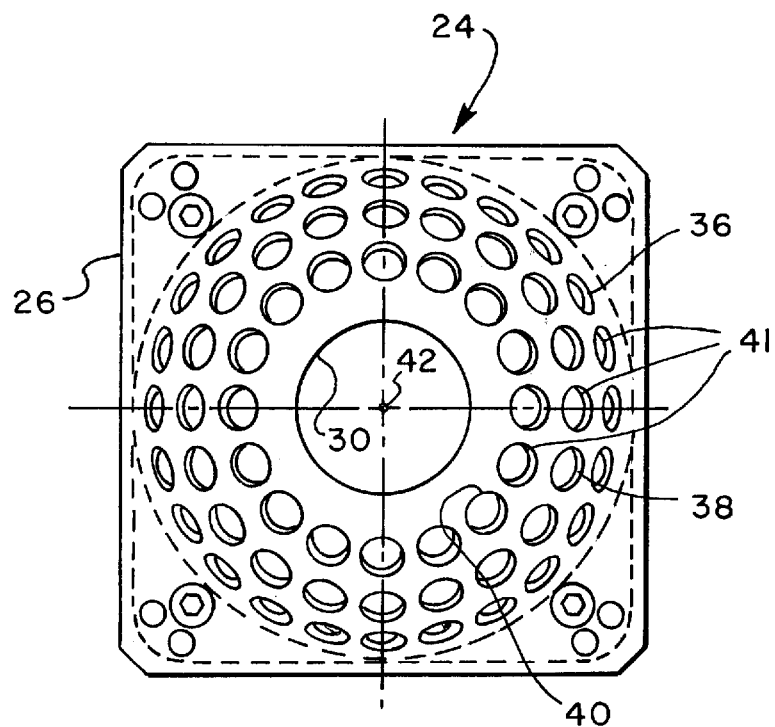
FIG. 2 is a plan view of a dome-shaped lighting array in accordance with one embodiment of the invention.
Figure 3:
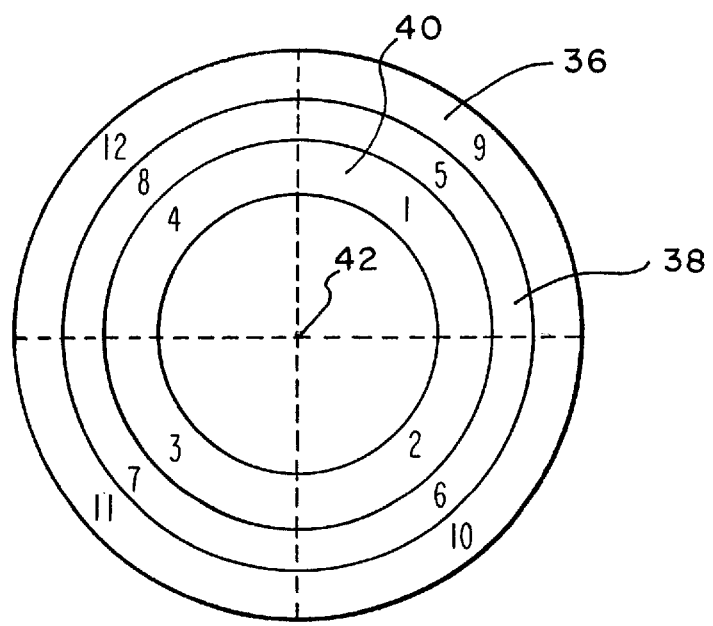
FIG. 3 is a diagram illustrating the number of segments of the lighting array shown in FIGS. 1 and 2 which are independently controllable in accordance with one embodiment of the invention.

Referring also to FIG. 2, the lighting array 24 includes a suitable, somewhat dome-shaped annular support member 34 disposed within the housing 26 and operable to support three circular arrays 36, 38 and 40 of light emitting elements, preferably light emitting diodes (LEDs) 41, which are arranged concentrically about a central axis 42, which is also the central axis of the aperture 30. The three arrays 36, 38 and 40 of LEDs may each be subdivided into plural segments of one or more LEDs 41, as indicated by the diagram of FIG. 3. The inner ring array 40 is divided, by way of example, into segments 1 through 4, the intermediate ring array 38 is divided into segments 5 through 8 and the outer ring array 36 of LEDs is divided into segments 9 through 12, as indicated. Each of the segments, which comprises one fourth of a circular arc, may be further subdivided into additional segments, if desired. As shown in FIGS. 1 and 2, the housing 26 has a substantially open bottom side to allow light emitted by the arrays 36, 38 and 40 of LEDs 41 to project onto the package 22 or any article which is placed under the dome-shaped support structure 34 for the LED arrays. The LED lighting array 24 may be suitably mounted on a machine vision apparatus together with the camera 32 so that a transport path for circuit packages 22 will place each package in the position shown in FIG. 1 to be fully illuminated by the array 24.

Figure 4:
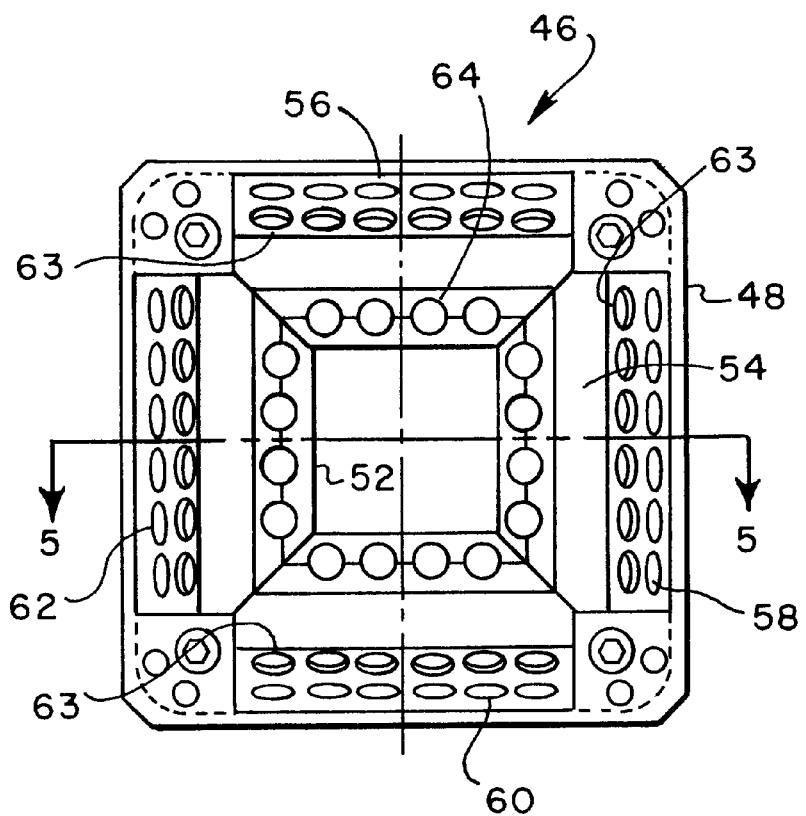
FIG. 4 is a plan view of an alternate embodiment of a lighting array in accordance with the invention.
Figure 5:
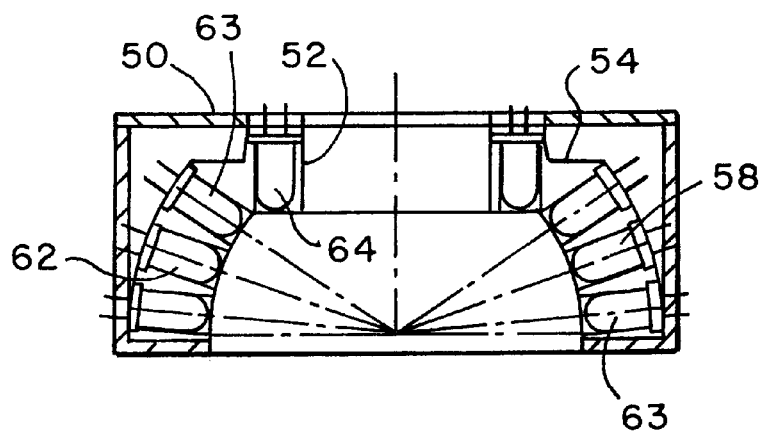
FIG. 5 is a section view taken along the line 5—5 of FIG. 4 showing further details of the alternate lighting array.

Referring briefly to FIGS. 4 and 5, an alternate embodiment of an LED lighting array for use in conjunction with the adaptive lighting system 20 is illustrated and generally designated by the numeral 46. The lighting array 46 includes a generally rectangular box shaped housing 48, having a top wall 50 in which a central rectangular aperture 52 is formed. The bottom side of the housing 48 is essentially open like the housing 26. A support structure 54 is disposed in the housing 50 and supports four circumferentially spaced linear arrays of LEDs indicated by numerals 56, 58, 60 and 62 and an inner rectangular ring array 64 around the aperture 52. Each of the LED arrays 56, 58, 60 and 62 includes three rows of LEDs 63, as shown. The LED array 46 may be used in place of the LED array 24, if desired.

Referring again to FIG. 1, the lighting system 20 is adapted to be operated by a digital computer or central processing unit 66, which includes a plurality of components, including a so-called frame grabber circuit 68, a programmable processor 70, a memory circuit 72 and a programmable light intensity control circuit 74. The light intensity control circuit 74 interfaces with a suitable input/output circuit or card 76 interconnected with the processor 70 and the programmable light intensity control circuit 74 for operation of same to vary the light intensity of the segments of the LED arrays 36, 38 and 40 to provide a suitable illumination and contrast between the package 22 so that the camera 32 may capture a high resolution image of the package 22 for various purposes known to those who are skilled in the art.

Figure 7A:
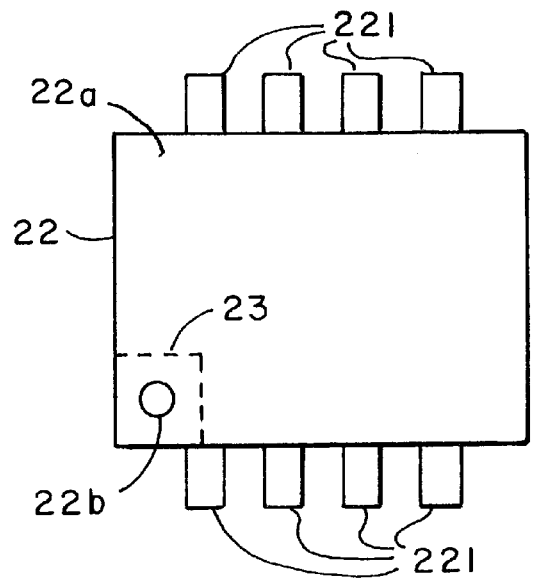
FIGS. 7A and 7B illustrate respective integrated circuit or semiconductor packages having package identifying indicia thereo.
Figure 7B:
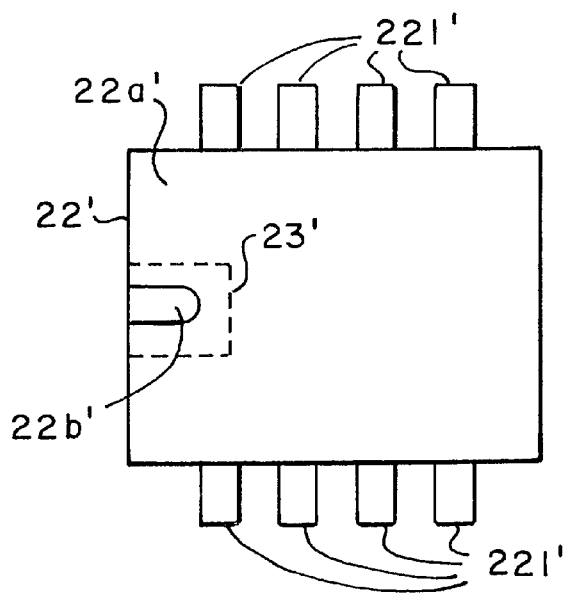

Semiconductor packages operable to be inspected by a vision apparatus including the lighting system 20 are usually provided with a preselected indicia on the surface 22a, FIG. 1. For example, as shown in FIG. 7A, a representative example of surface indicia is shown on surface 22a of a semiconductor package 22 comprising a small dimple or depression 22b in the surface 22a in the lower left corner, as indicated. Another example is shown in FIG. 7B wherein a semiconductor package 22' has a surface 22a' on which a notch-shaped depression 22b' is formed midway between opposite sides of the package body. When a package 22 or 22' is presented for inspection under the lighting array 24, the camera 32 obtains an image within a defined window 23 or 23', see FIGS. 7A and 7B, which is recorded by processor unit 66 and memory 72 is queried to identify the type of package being inspected. The light intensity adjustment is then carried out for capturing a desired image of the package 22 or 22' for inspection purposes or the like based on measurement taken from windows 23 or 23' or from the entire package including sets of leads 221 or 221'.

Figure 8:
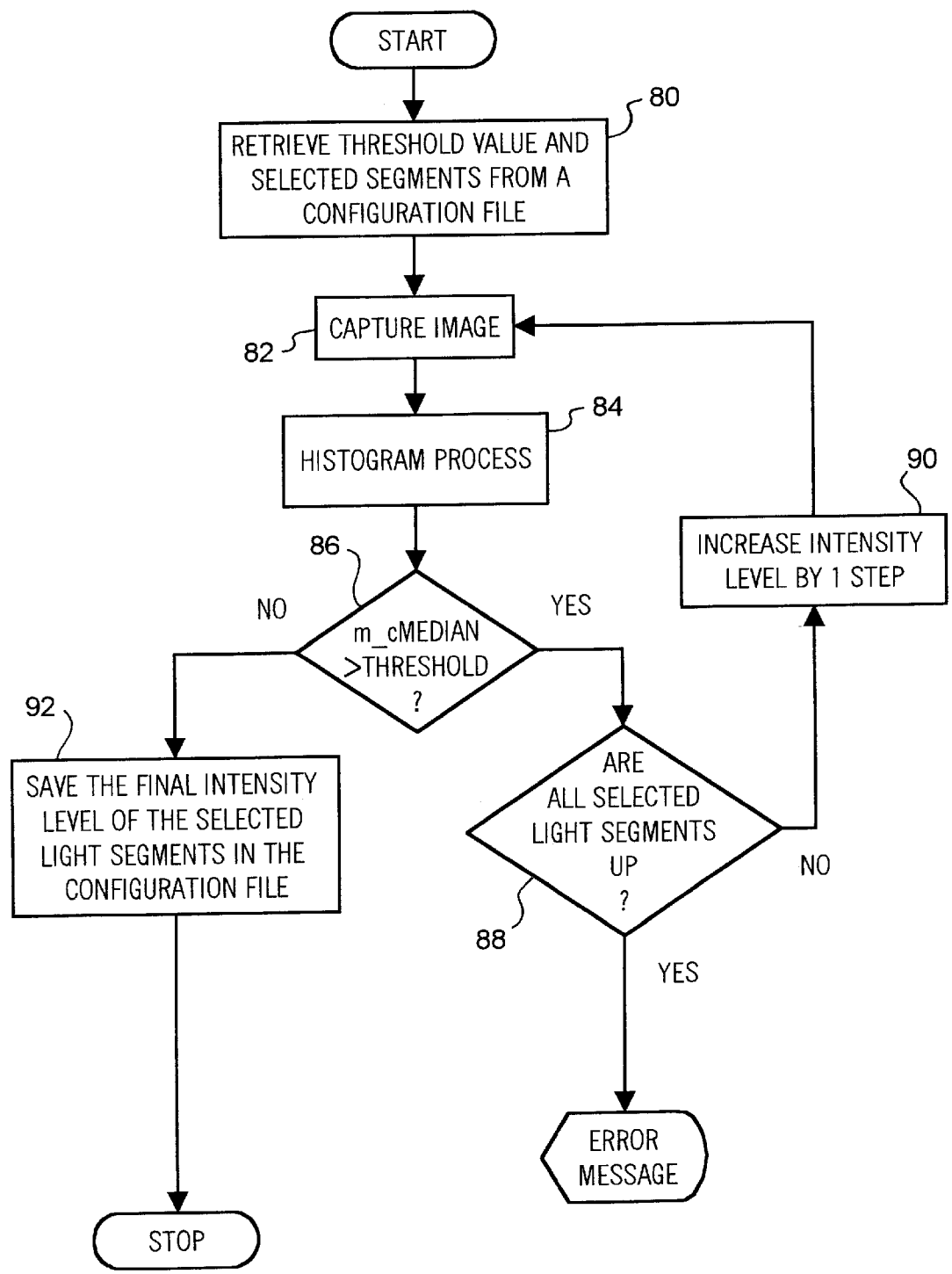
FIG. 8 is a flow chart showing certain steps in a method of operation of the adaptive lighting system of the invention.

Referring briefly to FIG. 8, there is illustrated a flow chart indicating the basic steps that the processor 66 takes to adjust the light intensity emitted by the array 24. The steps indicated in FIG. 8 include a histogram process which is described further herein. Basically, the processor 66 is programmed to calculate a histogram or a pixel intensity distribution of a specified source buffer and store the result in a specified histogram result buffer. The source buffer is derived from the defined windows 23 or 23' on a captured image of a package. If the median gray value of the camera pixel intensity distribution for camera 32 is less than a predetermined threshold value for a particular type of semiconductor package being viewed, and a predefined set of light segments is not already energized to full intensity the light intensity emitted by the selected segments is then increased a predetermined incremental amount and another image is captured. This process is repeated until the median gray value of the pixel intensity distribution is substantially equal to the predetermined threshold value. In this instance, the final intensity level of the selected light segments is saved to a configuration file for future use in inspecting packages of the same type.

Accordingly, with regard to FIG. 8, the basic steps in the process of capturing a well defined image of a package 22 or 22', comprise preconditioning the processor 66, when a known type of package is to be inspected, to retrieve a threshold value of image intensity and selected lighting array segments to be used for illuminating the package from a configuration file stored in the processor memory 72, as indicated by step 80 in FIG. 8. Alternatively, the processor 66 may be operated to retrieve the image intensity threshold value and selected lighting segments information upon the camera 32 and processor 66 recognizing the package type from obtaining an image of the package identifier indicia 22b or 22b', for example. Accordingly, the lighting system 20 may be operated in accordance with the method of the invention wherein the start of the operation is initiated by a package 22 presenting itself in viewing range of camera 32 to cause the camera and processor unit 66 to provide a trigger signal from frame grabber 68 to control circuit 74. With a known type of package presenting itself in view of camera 32 a trigger signal to initiate operation of control circuit 74 may be responsive to a sensor, not shown, associated with vision apparatus 18 which senses when the known type of package has been positioned for capturing an image with camera 32. In either case an image of a package to be inspected is captured by the camera 32 with the lighting array 24 illuminating the package in accordance with preselected lighting array segments operating at preselected light emitting intensities. The image capture step is indicated at step 82 in FIG. 8.

The next step in the process is the histogram process which is indicated at step 84 in FIG. 8. The histogram process includes the provision of a histogram of the intensity distribution of the camera pixel values for the camera 32 of an image of a particular semiconductor package. The median gray value of the accumulated histogram is selected as the threshold level of the image intensity distribution. In operating an adaptive lighting system, such as the system 20, when a known package type is to be processed by an inspection system including a machine vision apparatus, such as the apparatus 18, the threshold value or the median value of the pixel intensity distribution is retrieved from a configuration file and compared with a median value of pixel intensity distribution at a minimum intensity setting of the lighting array 24 using the predetermined lighting segments for inspecting the semiconductor package in question. This threshold value for good image contrast is retrieved from the configuration file and compared with the median value at the minimum light intensity setting and, if the median value is greater than the threshold value, the light intensity level is increased and a new image is captured of the semiconductor package of the type in question.

The median value of the accumulated histogram including the newly processed image is computed and compared again with the threshold value. This process is repeated at different incrementally increasing light intensity levels for the lighting segments selected until the median value reaches, approximately, the threshold value. The final light intensity setting at this condition of median value versus threshold value is saved to the aforementioned configuration file in the memory 42, for example, for the particular package type. This setting then is used in the next lot of packages of a similar type to be inspected by an inspection system, for example, using the machine vision apparatus 18, for example.

At the start of inspection of the next lot of semiconductor packages, a verification process is performed to determine if the median value of the image remains close to the threshold value so that the inspection process can be carried out. During the verification process, however, if the median value is far from the threshold value, the process just described is performed again starting from the minimum intensity level of the lighting array segments being energized until the above-mentioned optimum setting is reached. The verification process is considered necessary in order to adapt the lighting array to properly illuminate the surface of the package in question.

Referring further to FIG. 8, when the median gray value determined by the histogram process exceeds the threshold value obtained from step 80, at step 86, and all selected lighting segments are energized at maximum intensity an error message is indicated to the system operator in accordance with step 88. If all selected lighting segments are not at maximum intensity, as indicated from the configuration file, then the intensity of each of the operating lighting segments is increased by one "step" or increment, as indicated at step 90, and another image is captured, and the histogram process carried out. Once the median gray value obtained in the histogram process is substantially equal to the threshold value the final intensity level of the selected lighting segments is saved to the configuration file for the next inspection process for the same type of package as described, and as indicated in step 92.

Referring now to FIGS. 6A through 6G, there is illustrated a schematic diagram of the programmable intensity control circuit 74 for controlling the intensity of various segments of the lighting array described above and shown in FIGS. 2 and 3. The particular control circuit 74 shown in drawing FIGS. 6A through 6G is designed to provide selection of multiple LED segments up to a maximum of sixty-four segments and each segment can have its light output intensity programmed for operation at up to sixty-four incremental intensity levels. Moreover, each LED segment is driven by a constant current source which provides an option for strobe or non-strobe operation of the lighting array 24. Still further, the circuit 74 is capable of high speed switching within a switching time of about 200 nanoseconds between respective sets of LED segments which have been preprogrammed to operate at the switched intensity levels.

In this way, the lighting array 24 may provide for rapidly capturing two images of a package 22 by the camera 32 at different lighting intensity settings of the array 24.

Figure 6A:
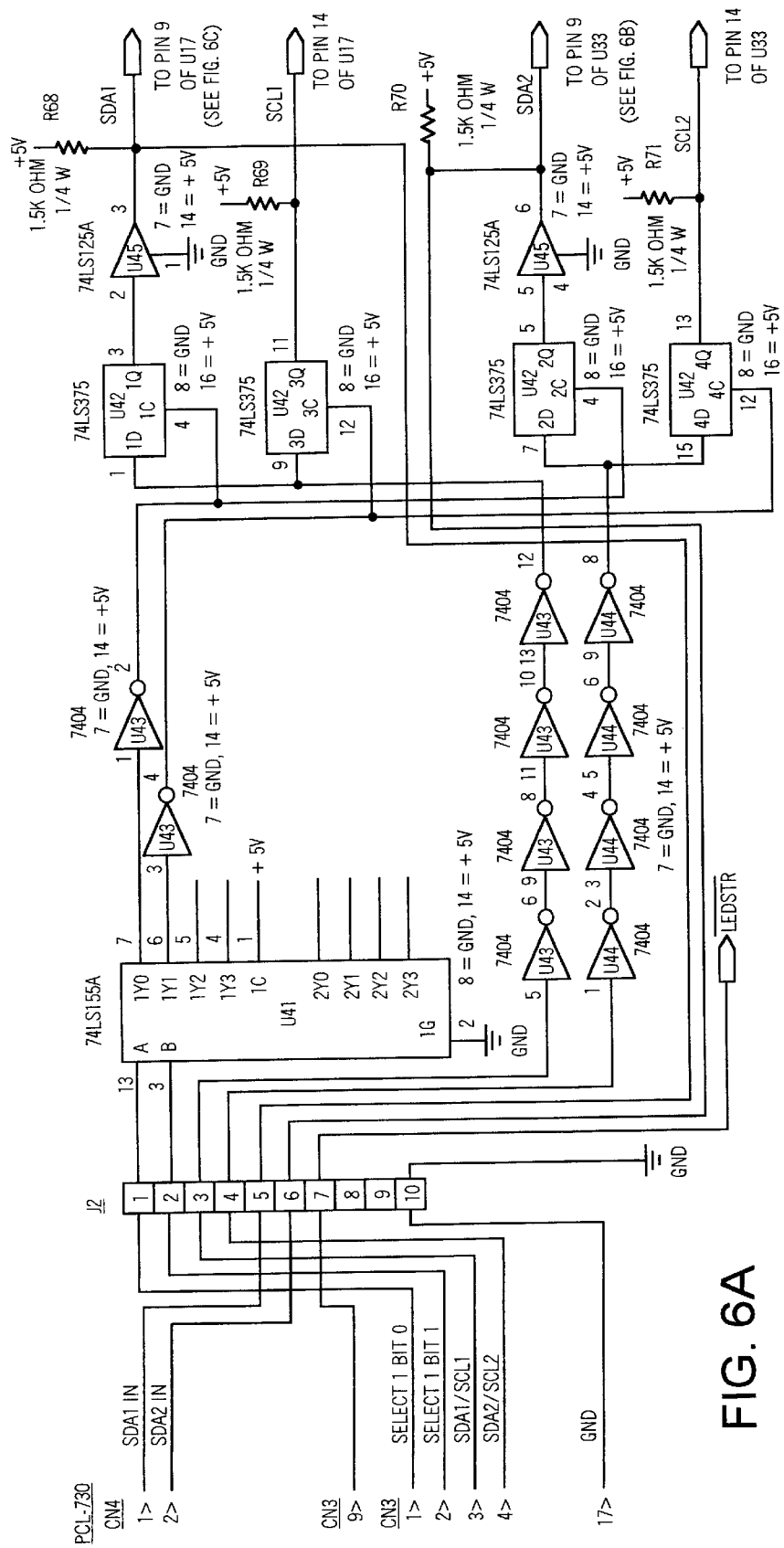
FIGS. 6A through 6G comprise a circuit diagram for a programmable light intensity control circuit in accordance with the invention.

Referring briefly to FIG. 6A, the control circuit 74 is adapted to be coupled externally with I/O card 76 which is inserted in a suitable card slot in a conventional central processing unit such as an IBM PC-AT digital computer, for example. The control circuit 74 includes a decoding circuit, FIG. 6A, including a decoder/multiplexer U41 which is operably connected to bi-stable latches, as shown and designated U42. These circuit elements are connected between the input/output circuit 76 and non-volatile digital potentiometers indicated by the designators U17 through U33, see FIGS. 6B through 6G also. The potentiometers U17 through U33 may be of a type available from Xicor, Inc., Milpitas, Calif., as their Part No. X9241WP. The control bits used and the logic of the serial outputs to the digital potentiometers are shown in FIG. 9.

As shown in FIGS. 6A through 6G, signal paths SCL1 and SCL2, FIG. 6A, are clock inputs to the potentiometers U17 through U33 to clock data into and out of these circuits. Signal paths SDA1 and SDA2 are bi-directional and are used to transfer data into and out of the potentiometers U17 through U33. Signal paths SCL1, SCL2, SDA1 and SDA2 and power paths VH, VL and VD, VS carry numerical correlation prefixes between FIGS. 6C and 6G for convenience. Potentiometers U17 through U32 are assigned unique addresses through terminals A0, A1, A2, A3, respectively. The address assignments are indicated in FIG. 10.

Potentiometers U17 through U32 are connected to provide, by way of example, sixty-four resistor arrays each composed of sixty-four wiper elements. The position of a wiper element for an array is controlled by the user through signal paths SDA1 and SCL1. Control of a wiper element through the two wire serial interface may be carried out using published data available from Xicor, Inc. for the X9241WP non-volatile digital potentiometer.

Figure 6B:
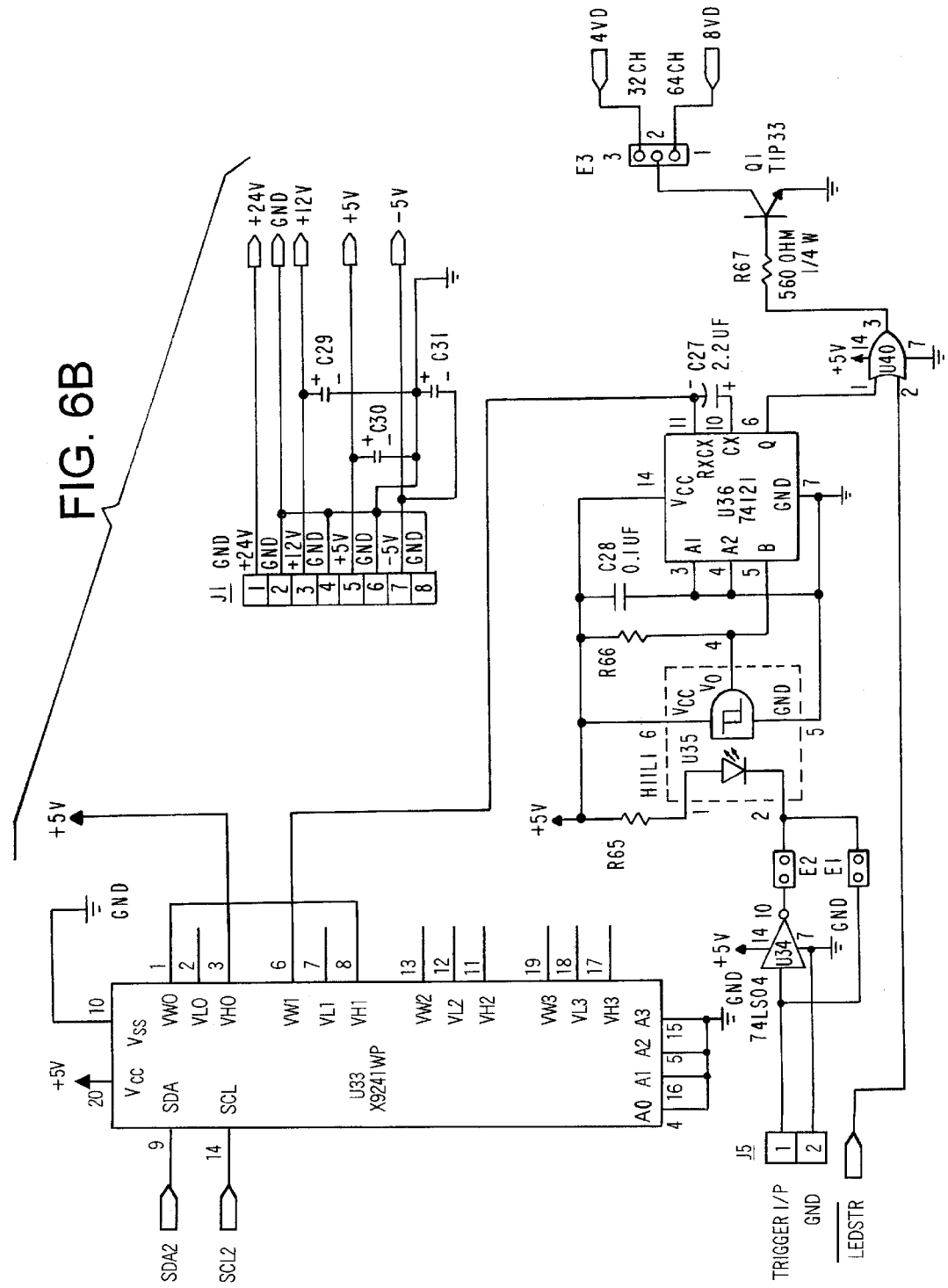

For operation of the lighting array 24 in a strobe mode, circuit U33, FIG. 6B, provides for two resister arrays cascaded to provide a variable resistance to a timing circuit for a monostable multi-vibrator U36. The position of the wiper element on each array segment is controlled by the user through signal conductors SDA2 and SCL2. The timing circuit for multivibrator U36 is determined by the cascaded resistances and capacitance C28 to provide a desired output signal pulse duration at output terminal Q of the multivibrator. This pulse is obtained when terminal B is being edge triggered by an input trigger signal from processor 70 by way of trigger input terminal J5, hex inverter U34 and opto-isolator U35. During the "on" pulse duration, power transistor Q1, FIG. 6B, is activated to energize all the LED segments of array 24 simultaneously. The strobe mode may be enabled through connector J2 and signal path LEDSTR, FIGS. 6A and 6B, from processor 70. FIG. 6B also illustrates a schematic for a multi-terminal connector J1 which provides for the appropriate power paths of plus 24 volts, plus 12 volts, plus 5 volts and minus 5 volts from a suitable source, not shown. Capacitors C29, C30 and C31 are connected as shown to provide suitably stable voltages at the respective levels indicated.

Figure 6C:
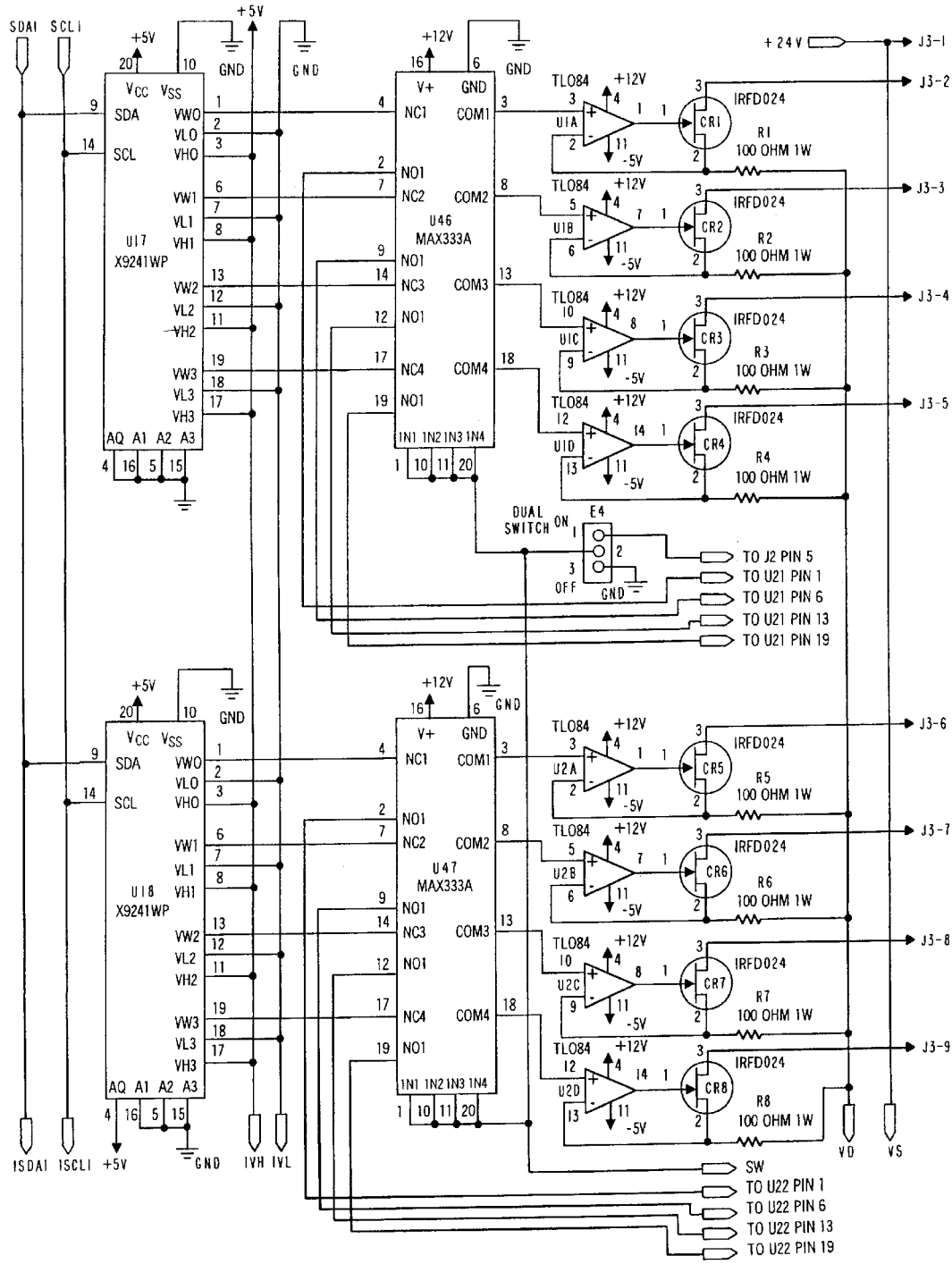
Figure 6D:
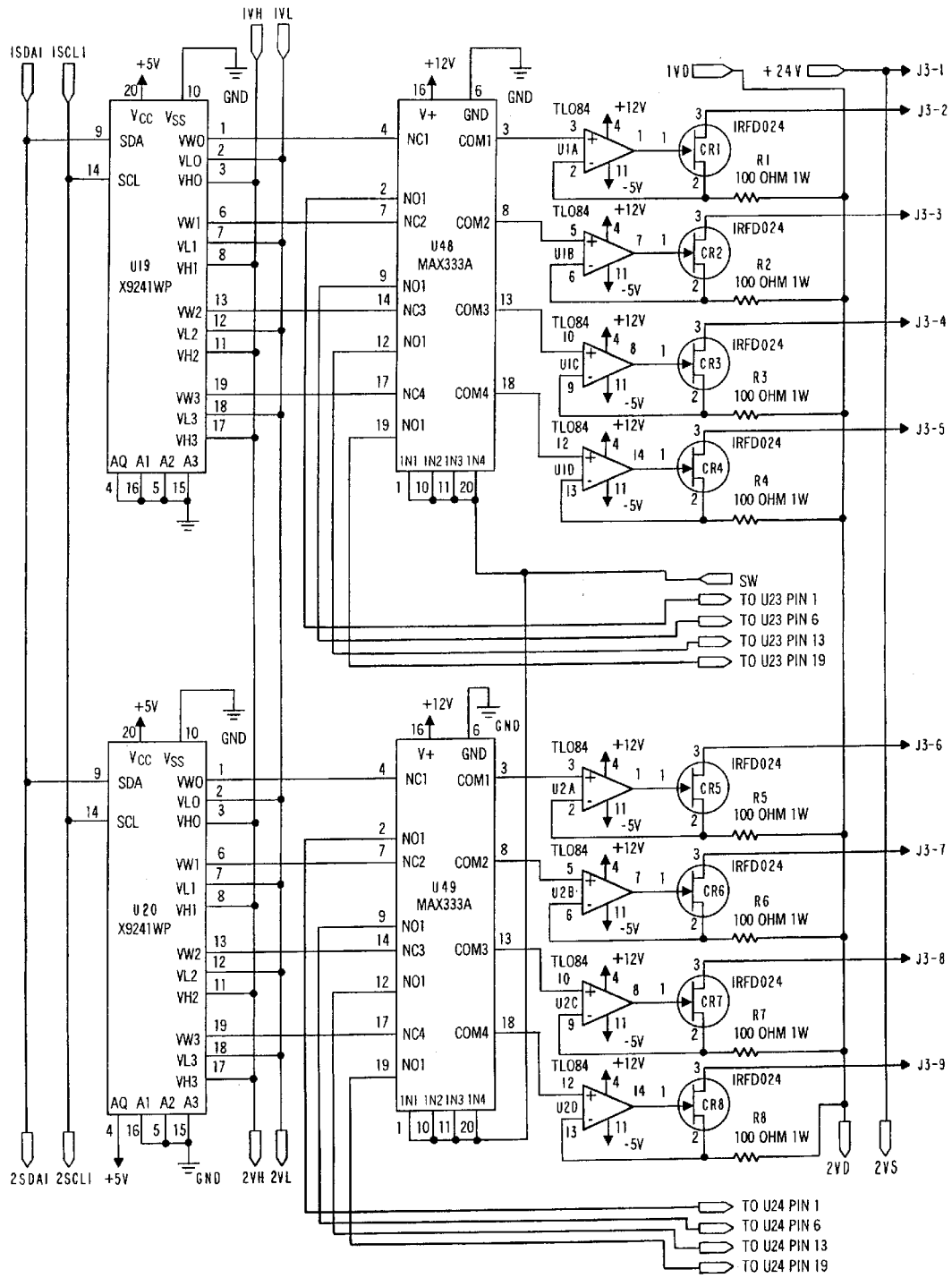
Figure 6E:
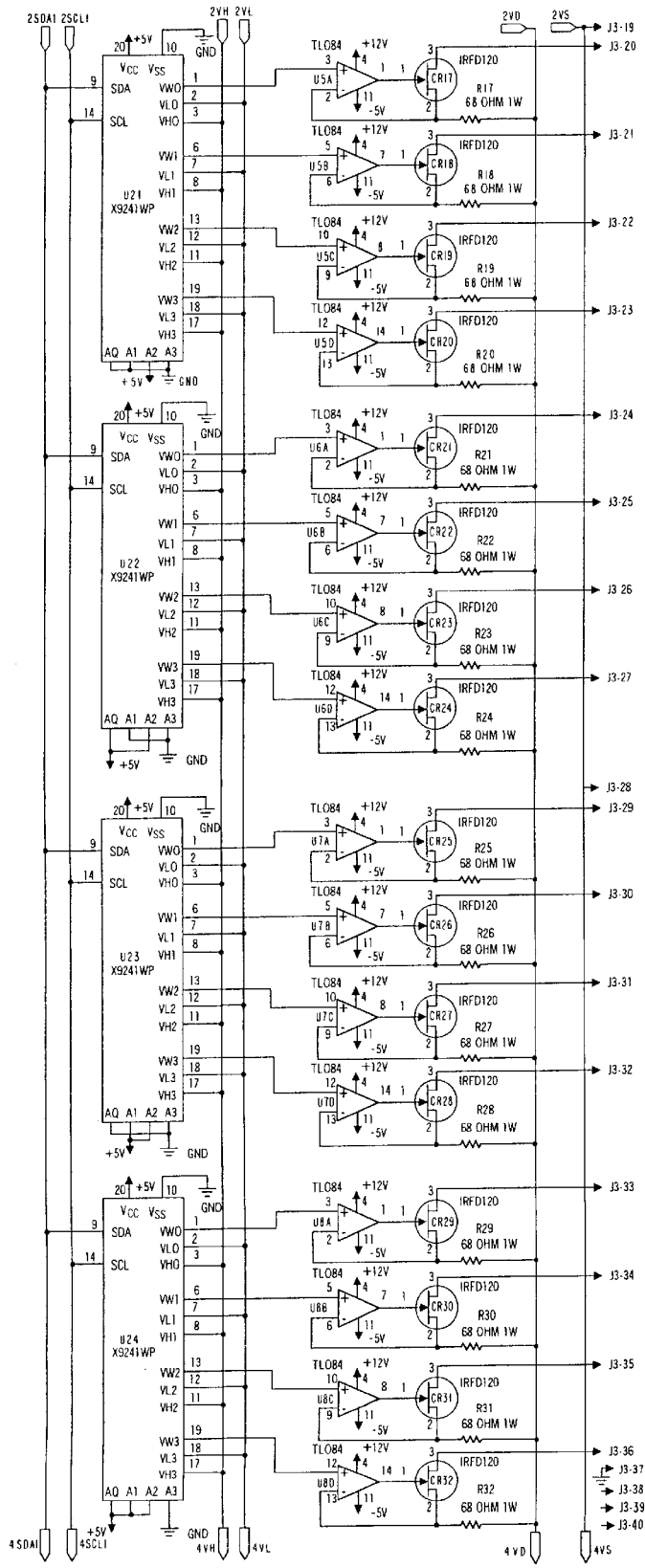
Figure 6F:
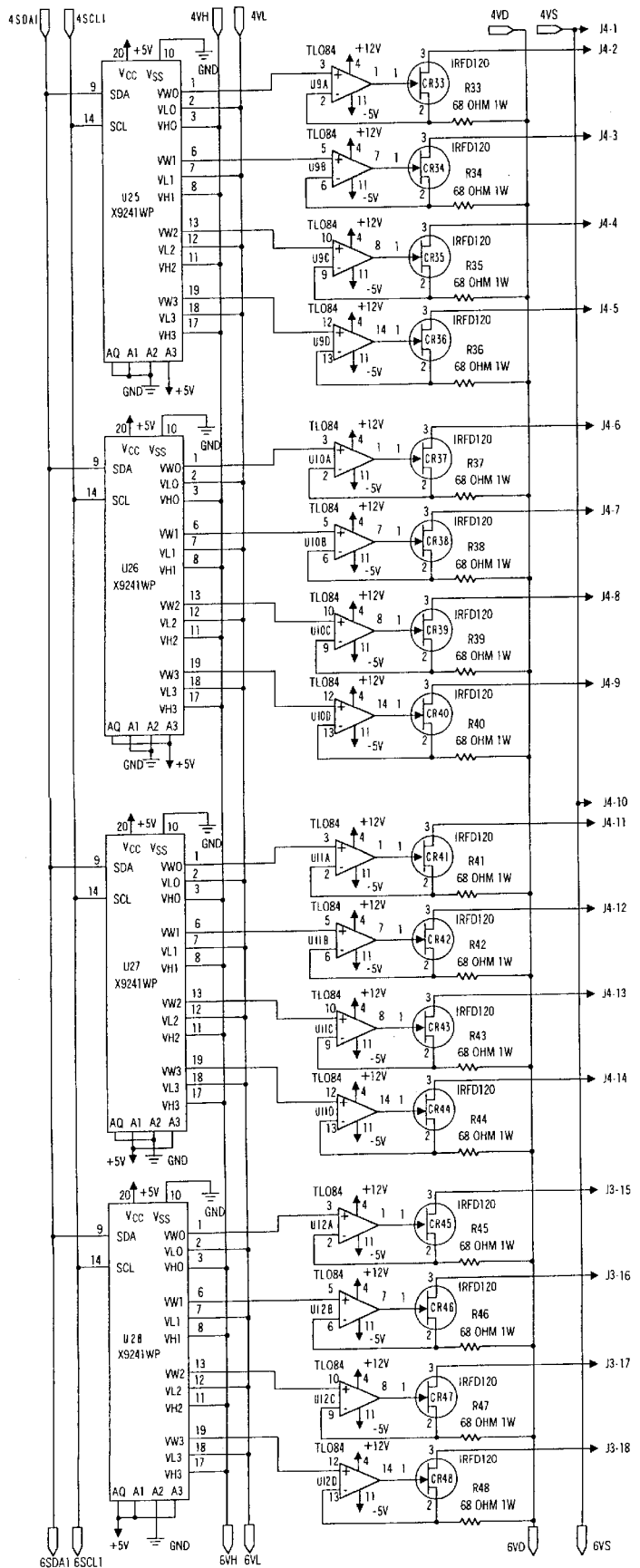
Figure 6G:
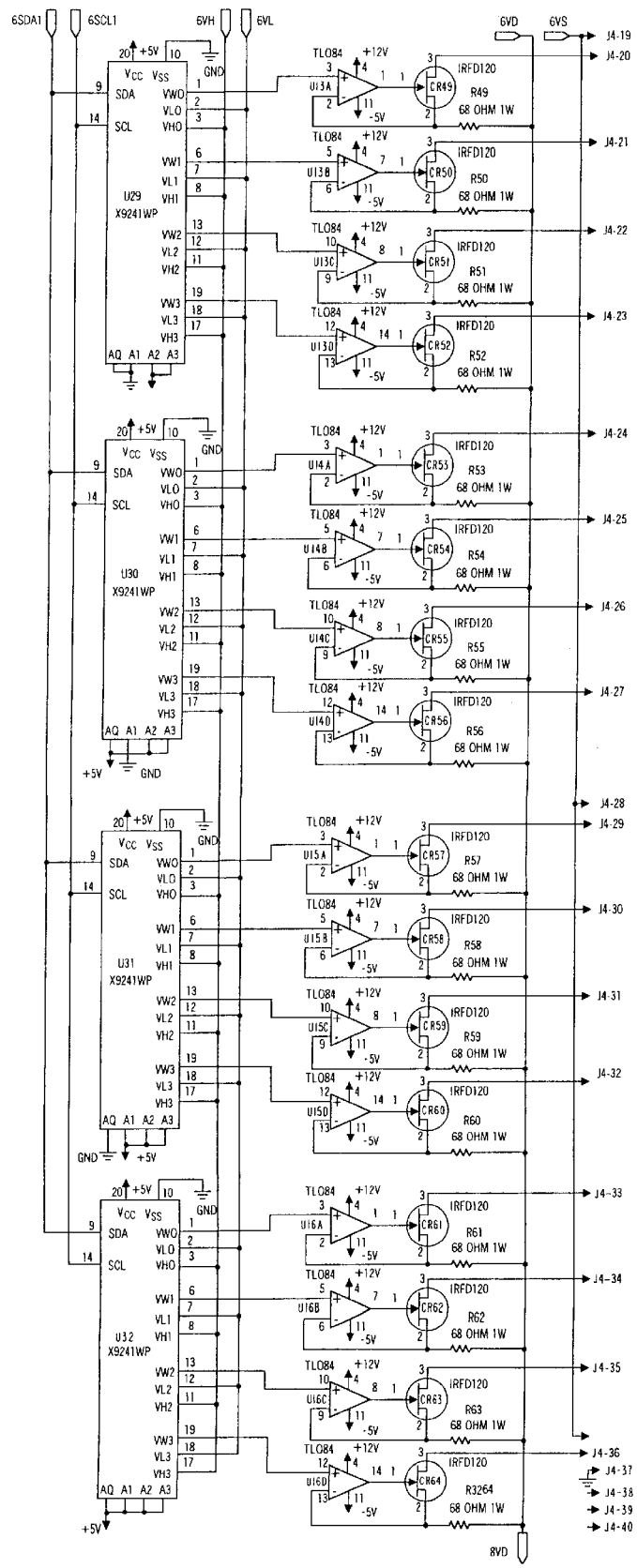

Another important aspect of the present invention is included in the control circuit 74 and provides for operation of high speed switching between two "banks" or sections of LED segments so that the light intensity pattern of illumination on a package 22, for example, may be rapidly switched from one to another to allow image capture of each pattern by the camera 32 for comparison purposes. In this regard, as shown in FIGS. 6C and 6D, the output signals from the potentiometers U17, U18, U19 and U20 are transmitted through respective SPDT CMOS analog switches U46, U47, U48 and U49. Switches U46, U47, U48 and U49 are also operably connected to the output pins indicated in the circuit diagrams of potentiometers U21, U22, U23 and U24, respectively. Switches U46, U47, U48 and U49 are actuated through a signal from processor 70 by way of a suitable signal path through connector J2 shown in FIG. 6B to the jumper socket E4 shown in FIG. 6C. Each of switches U46, U47, U48 and U49 is operable to receive a switching signal via the above-described path as indicated in FIGS. 6C and 6D. Accordingly, the settings of the potentiometers U17, U18, U19 and U20 may be imposed on either the lighting segments normally connected to these potentiometers or the lighting segments normally connected to the potentiometers U21, U22, U23 and U24 to provide two different lighting patterns for illuminating a package, such as the package 22. The lighting pattern switching speed may be about 200 nanoseconds using the components of the control circuit 74. In this way, the camera 32 may capture two images rapidly at two different light intensity settings and whereby the processor unit 66 may compare the images for identification and inspection purposes, for example.

Moreover, each LED segment is provided with a constant current source which consists of operational amplifiers U1A to U1D through U16A to U16D as shown in FIGS. 6C to 6G, which amplifiers are respectively coupled with power MOSFETS CR1 to CR64. The limiting current for each segment is set by a 100 ohm resistor, R1 through 64. The output signals from the control circuit 74 and power signals are imposed on the segments of LEDs 41 of the array 24 through multi-conductor connectors J3 and J4, see FIGS. 6C through 6G.

Figure 11A:
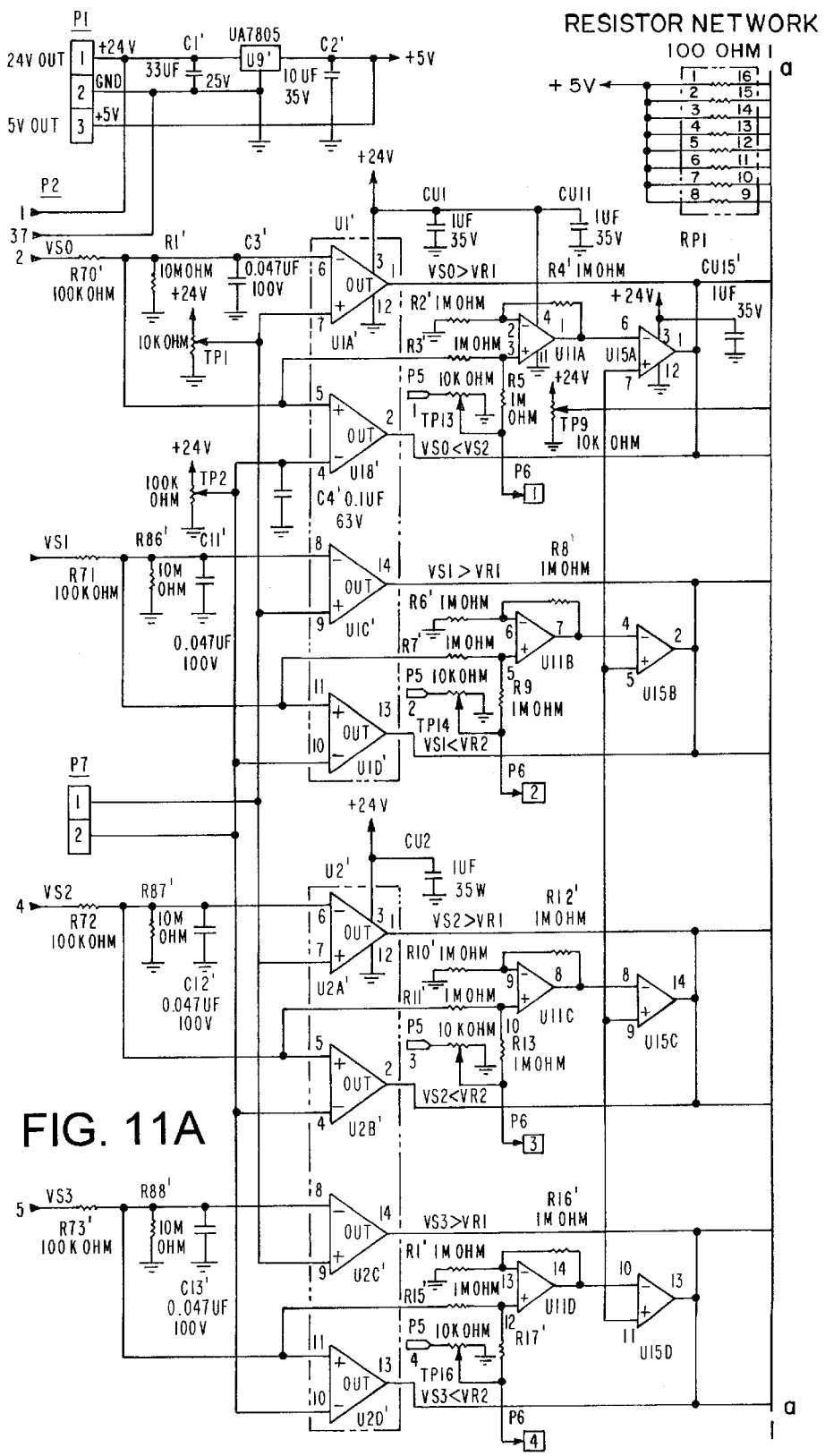
FIGS. 11A and 11B comprise a circuit diagram of a portion of a light failure module for the lighting system of the invention.
Figure 11B:
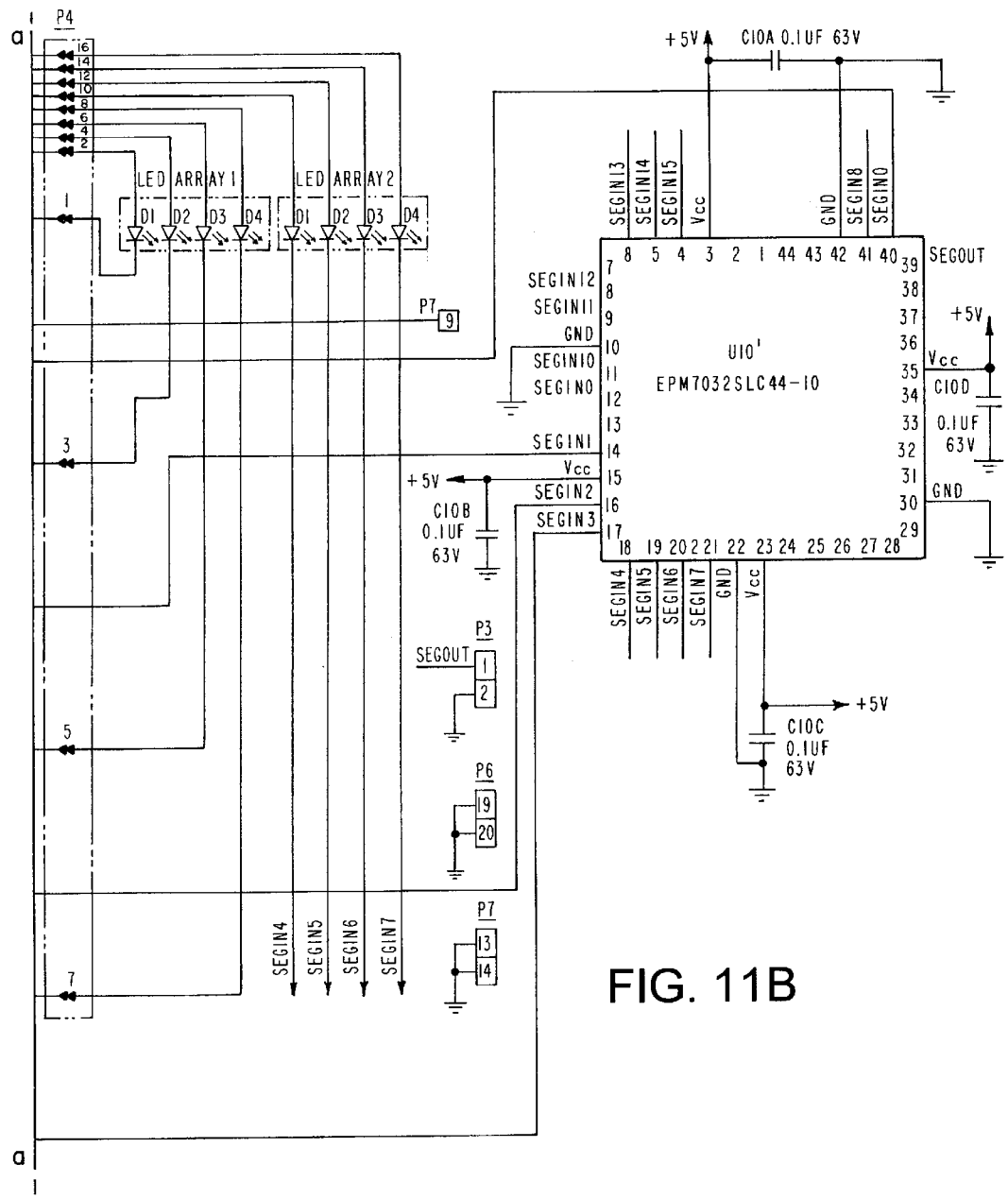

Referring now to FIGS. 11A and 11B, these figures are intended to be read together when joined at line a—a. The components identified in FIGS. 11A and 11B which bear reference designations the same as shown for components in FIGS. 6A through 6G are differentiated by the sign. FIGS. 11A and 11B illustrate a diagram of a portion of a circuit for a light failure "module" for monitoring the failure of any of the LEDs of a segment of the LED array 24, for example. The circuit diagram of FIGS. 11A–11B illustrate the light failure module or circuitry for two LED arrays or segments. The circuitry may be repeated for the total number of segments present in an LED array such as the array 24. As shown in FIG. 11A, connector P2 receives a twenty-four volt DC power supply from the system 20 and steps this voltage to a five volt DC supply at regulator U9'. The circuit shown in FIG. 11B includes a programmable logic device U10' which also operates on a five volt DC supply and is programmed to generate alarm signals at connector P3. Multiple voltage signals are input at connector P2 through, for example, conductors VS0, VS1, VS2, and VS3, which are, respectively, operably connected to pin 3 of MOSFETS CR1 through CR8, respectively, for example.

By way of example, viewing FIG. 11A, a voltage signal to LED array 1 and LED D1 from voltage comparator U1A will signal a "failure" in the light segment associated with MOSFET CR1, FIG. 6D, if there exists an open circuit condition or reversed connections to the LED light segment associated with MOSFET CR1. The input voltage signal from MOSFET CR1 to comparators U1A and U1B is compared to a reference voltage at potentiometers or trimmers TP1 and TP2. If the input voltage is greater than reference voltage VR1 or less than voltage VR2, see FIG. 11A, the LED indicator D1 turns on indicating a light failure on the associated segment of the LED lighting array. Similar circuitry applies to each light segment.

Input signals are also provided at connectors P5 from constant current voltage provided at pin 2 of MOSFETS CR1 through CR16, respectively. These constant current voltages are input to an adder circuit using an op amp U11A, as shown by way of example for the circuit associated with MOSFET CR1, FIG. 11A. Each op amp circuit combines the light segment voltage with the constant current voltage. The resultant voltage is input to a comparator U1SA, for example, to detect a failure of an LED in a segment of the lighting array 24 resulting in a short circuit. The resultant voltage is compared with a reference voltage at potentiometer or trimmer TP9, for example. If the resultant voltage is greater than the reference voltage, the indicator D1 turns on also indicating a light failure in the associated LED lighting segment. As indicated above, this circuitry applies to each of the light segments of the LED lighting array 24 and may be repeated for up to the 64 segments referenced with regard to FIG. 6C through 6G. Those skilled in the art will appreciate that the light failure module described and shown provide an important and advantageous feature for the adaptive lighting system 20.

Figure 12:
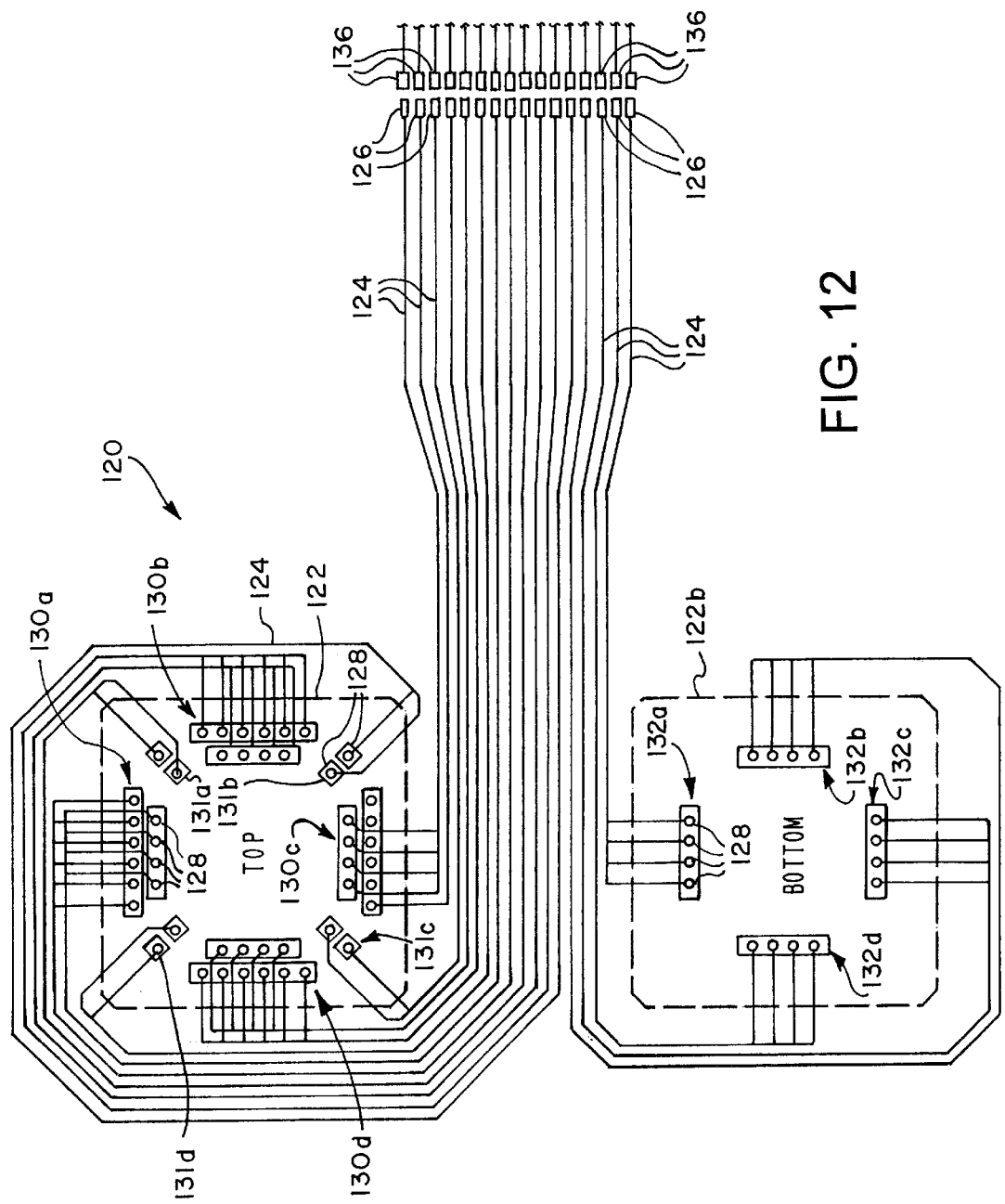
FIG. 12 is a diagram of an alternate embodiment of a lighting array in accordance with the invention.
Figure 13:
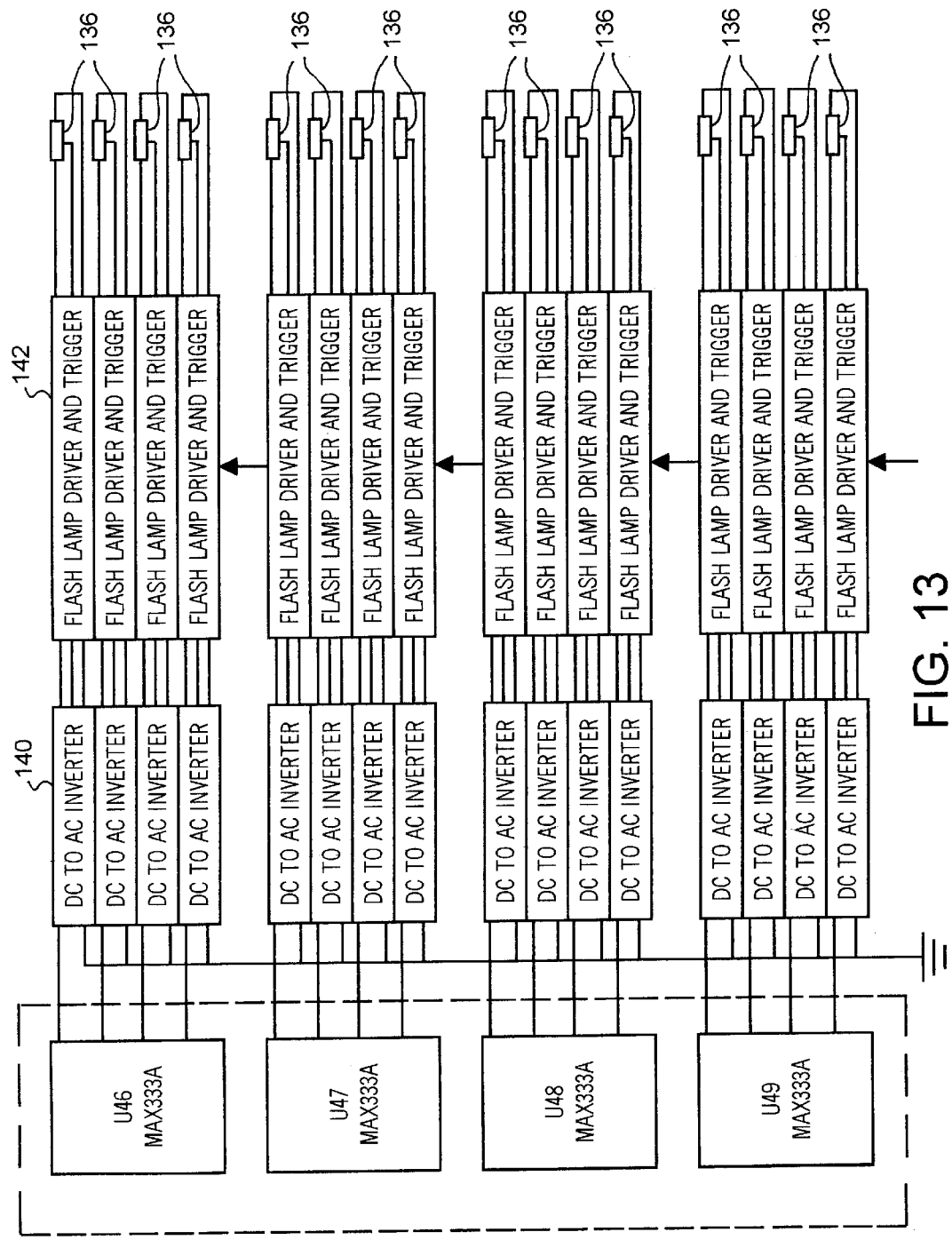
FIG. 13 is a block diagram of the major components of the lighting array of the embodiment shown in FIG. 12.

Referring now to FIGS. 12 and 13, another embodiment of an adaptive lighting system in accordance with the invention is illustrated and generally designated by the numeral 120. The lighting system 120 may utilize an enclosure or housing 122 for supporting an array of fiber optic elements 124, each having a light input head 126, as shown in FIG. 12, and one or more light output heads 128 arranged in particular patterns, as illustrated, within the enclosure or support 122. The entire lighting array of system 120 may be made up of the optical fiber elements 124 having light input heads 126 and one or more light output heads 128 arranged as illustrated. In the exemplary system 120 shown in FIG. 12, four arrays of ten light output heads 128 are arranged in a rectangular pattern together with four arrays of two light output heads 128 interposed the arrays of ten output heads, respectively. This lighting array may be used in place of the lighting array shown in FIGS. 4 and 5, for example, and may be supplemented by additional arrays of four output heads 128 each disposed in a position beneath the semiconductor package to be inspected and suitably supported on a support member 122b, for example. The lighting array shown schematically in FIG. 12 may be used alone or used to supplement the light output of an array of LED light sources. As shown in FIG. 12, the opposed segments of ten light output heads 128 are indicated by numerals 130a, 130b, 130c and 130d and the intermediate arrays illustrated are indicated by numerals 131a, 131b, 131c and 131d. Other arrays or arrangements of the multiple light output heads 128 are possible. In like manner, the opposed arrays which may be disposed below the package are indicated by numerals 132a, 132b, 132c and 132d.

As further shown in FIG. 12 and FIG. 13, the optical fiber elements 124 are adapted to transmit light provided by multiple flash lamps 136 with at least one flash lamp arranged in proximity to a light input head 126 of an optical fiber element or bundle of elements 124. Sixteen flash lamps 136 are shown schematically in FIGS. 12 and 13.

As shown in FIG. 13, the flash lamps 136 are arranged in groups of four each for the exemplary system 120 and are operably connected to switches U46, U47, U48 and U49 by way of respective DC to AC inverter circuits 140 and corresponding flash lamp driver and trigger circuits 142, as illustrated generally by the block diagram of FIG. 13. Accordingly, the output signals from switches U46, U47, U48 and U49 are input to the circuits of FIG. 13 in place of the LED arrays connected to these switches as shown for the embodiment whose circuit is illustrated in FIGS. 6C and 6D. Accordingly, the flash lamps 136 are driven by the sixteen sets of flash lamp drivers and triggers which obtain variable DC output voltage signals from the potentiometers U17, U18, U19 and U20 by way of the switches U46, U47, U48 and U49 and by way of the DC to AC inverters 140. The flash lamps 136 may be provided as one of a type commercially available. A common input signal is provided to trigger all of the flash lamp driver and trigger circuits simultaneously. The DC to AC inverters 140 may also be one of a type commercially available.

Figure 14:
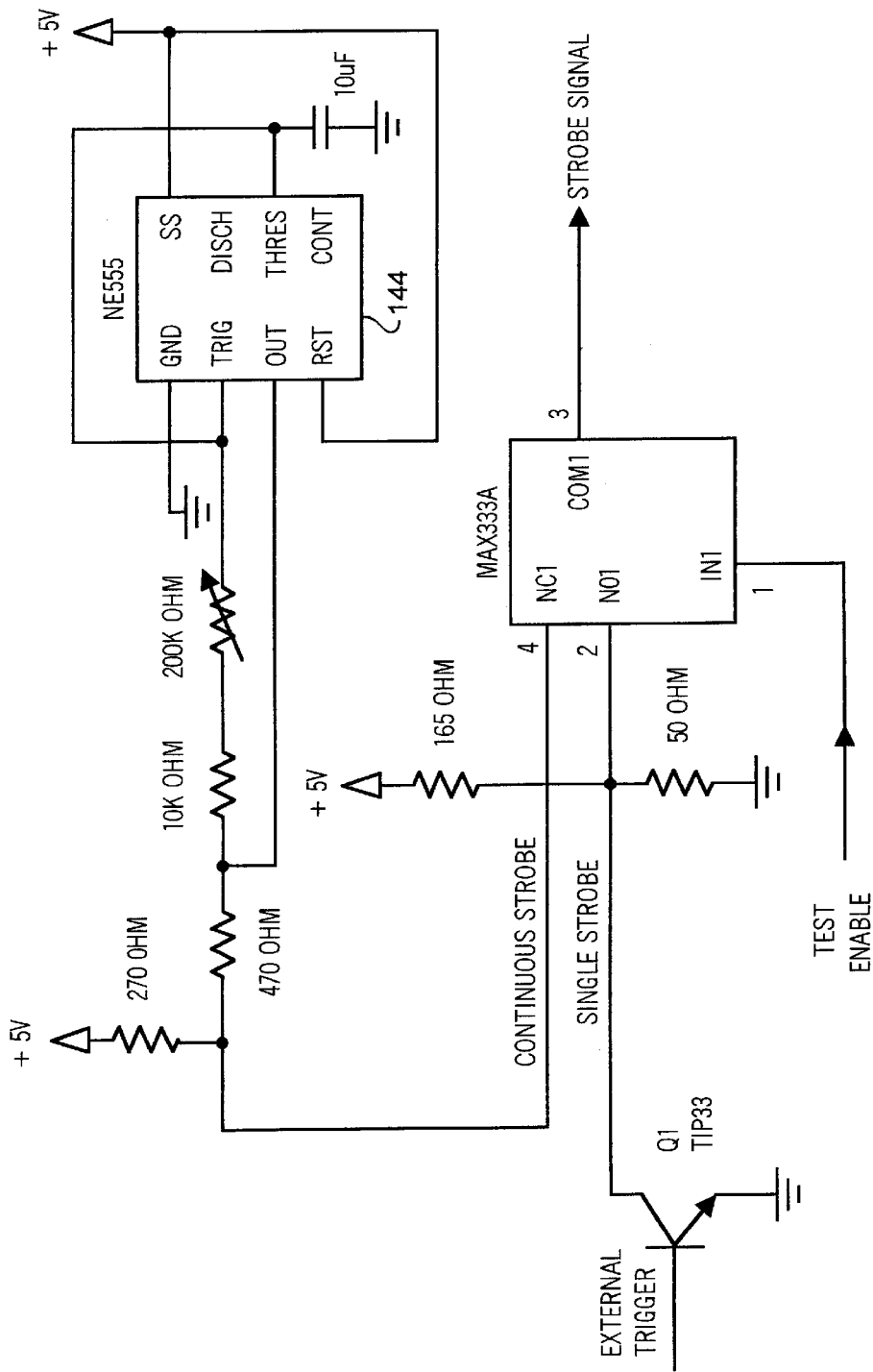
FIG. 14 is a detail schematic diagram of the switching and timing circuit for generating a signal to energize one of the flash lamp.

Referring now to FIG. 14, a more detailed schematic diagram is shown indicating how the flash lamp strobe signal may be generated. An external trigger signal may be generated by one of the light intensity programmable controllers U17, U18, U19, or U20 for each array segment which signal is transmitted through transistor Q1 in FIG. 14 and is input to pin NO1 of one of the switches U46, U47, U48 or U49, as the case may be. A test enable signal may also be imposed on one of the switches U46, U47, U48 or U49 at pin IN1. When the test enable signal is activated, a continuous strobe output signal, which may be varied in frequency from zero to twenty-five Hz, is provided at output pin COM1 for the respective switch U46, U47, U48 or U49. A timer circuit comprising, for example, a circuit 144 in FIG. 14 is connected to input terminal NC1 of the relevant switch U46, U47, U48 or U49. Accordingly, a single strobe output signal from switch U46, U47, U48 or U49 is provided when a test enable signal is inactive and an external trigger signal from a light intensity programmable controller is active. Conversely, when a test enable signal is input to one of the switches U46, U47, U48 or U49, a continuous strobe signal in a selected frequency range is provided at switch output pin COM1. The timers 144 are each controlled by an external resistor and capacitor circuit shown in FIG. 14.

Figure 15:
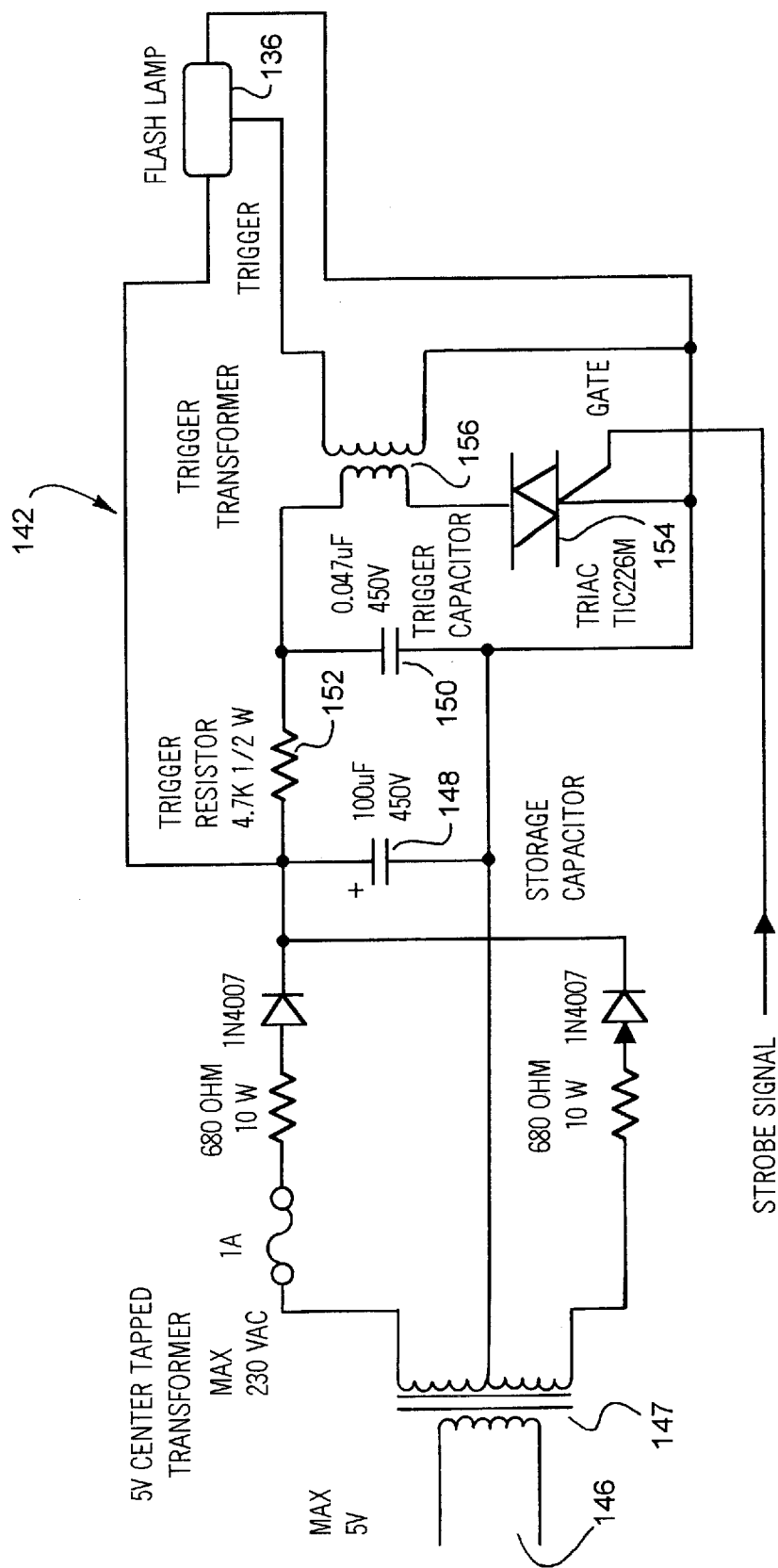
FIG. 15 is a detail schematic of a flash lamp driver and trigger circuit for the embodiment of FIGS. 12 and 13.

Referring now to FIG. 15, one of the flash lamp driver/trigger circuits 142 is illustrated. A variable voltage signal received from a DC to AC inverter 140 associated with a circuit 142 is connected to the primary side 146 of a center tapped transformer 147, as shown in FIG. 15. The winding ratio of transformer 147 is about 1:46. Variable secondary voltages charge storage capacitor 148 through the circuit, as shown in FIG. 15, to an RMS voltage of up to three hundred twenty five volts DC maximum. This voltage in turn charges trigger capacitor 150 throug trigger resistor 152. When a strobe signal of about one volt at twenty miliamps is present at the gate of triac 154 from the circuitry, shown in FIG. 14, for example, the trigger capacitor 150 will discharge through transformer 156 to energize flash lamp 136.

The operation of the adaptive lighting system 120 is believed to be understandable to those of ordinary skill in the art based on the foregoing description read in conjunction with drawing FIGS. 12 through 15.

The construction and operation of the adaptive lighting systems 20 and 120 are believed to be understandable to those skilled in the art from the foregoing description and taking into consideration the circuit diagrams of FIGS. 6C through 6G, FIGS. 11A and 11B and FIGS. 13 through 15, in particular.

A correlation table for certain ones of the circuit elements commercially available and not otherwise identified follows:

| Commercial Part No. | Ref. No. | Description | Mfr. |
| --- | --- | --- | --- |
| SN74LS155A | U41 | IC, DUAL 2-LINE TO 4 LINE DECODERS/ DEMULTIPLEXERS | TI |
| SN74LS375 | U42 | IC, 4-BIT BISTABLE LATCHES | TI |
| SN7404 | U43,U44 | IC, HEX INVERTERS | TI |
| SN74LS125A | U45 | IC, QUAD BUS BUFFERS WITH 3-STATE OUTPUTS | TI |
| TL084CN | U1-U16 | JFET INPUT OPERATION AHPLIFIERS | TI |
| X9241WP | U17-U33 | QUAD CMOS EEPOT, 10 K OHMS | XICOR |
| SN74LS04 | U34 | IC, HEX INVERTERS | TI |
| 585-292 | U35 | IC, OPTO-ISOLATOR, SCHMITT TRIGGER HIU | RS |
| SN74121 | U36 | IC, MONOSTABLE MULTIBRATORS WITH SCHMITT-TRIGGER INPUTS | TI |
| MAX333A | U46-U49 | IC, PREVISION QUAD SPDT CMOS ANALOG SWITCH | MAXIM |
| SN74LS32 | U40 | IC, QUAD 2-INPUT POSITIVE-OR GATE | TI |
| IRFD024 | CR1-CR64 | HEXFET POWER MOSFETS | INTERNATIONAL RECTIFIER |
| TP33 | QI | IC, NPN SILICON POWER TRANSISTOR | TI |
| 402-765 | U1-U16,U34,U36, U40,U43-U45 | IC SOCKET 14 PIN | RS |
| 402-771 | U41,U42 | IC SOCKET 16 PIN | RS |
| 402-793 | U17-U33 | IC SOCKET 2O PIN | RS |
| 402-743 | U35 | IC SOCKET 6 PIN | RS |
| 402-759 | U39 | IC SOCKET 8 PIN | RS |
| E19-2185 | CR1-CR64 | PIN TURNED | PROSPEC |
| LITTLE DEVIL | R1-R64 | RESISTOR 100 OHMS, 1W | OHMITE |
| LITTLE DEVIL | R65 | RESISTOR 620 OHMS, 1/4W | OHMITE |
| 131-312 | R66 | RESISTOR 3.3 K OHM, 1/4W | RS |
| LITTLE DEVIL | R67 | RESISTOR 56 C OHM, 1/4W | OHMITE |
| LITTLE DEVIL | R68-R71 | RESISTOR 1.5 KN OHM. 1/4W | OHMITE |
| 334-561 | E1,E2 | JUMPER LINK | RS |
| CC2.2F | C27 | CERAMIC CAPACITOR 2.2 $\mu$F | PROSPEC |
| CCO.1F | C28 | CERAMIC CAPACITOR 0.1 $\mu$F | PROSPEC |
| AK100/8 | J1 | CONNECTOR 8 WAY SCREW TERMINAL | ELECTROSPEED |
| AK100/10 | J2 | CONNECTOR 10 WAY SCREW TERMINAL | ELECTROSPEED |
| 458-370 | J3,J4 | CONNECTOR 40 WAY PLUG RIGHT-ANGLE PCB MOUNT | RS |
| AK100/2 | JS | CONNECTOR 2 WAY SCREW TERMINAL | ELECTROSPEED |
| ECO50F35 | C29 | ELECTROLYTIC CAPACITOR 33 $\mu$F, 35 V | PROSPEC |
| TCIO.35 | C30, C31 | TANTALUM CAPACITOR 10 $\mu$F, 35 V | PROSPEC |
| ML 104 | C1-C45 | MULTILAYER CAPACITOR 0.1 $\mu$F, 50 V | PROSPEC |
| AK100/15 | J6 | CONNECTOR 15 WAY SCREW TERMINAL | ELECTROSPEED |
| M7565-06 | E3,E4 | JUMPER SOCKET SINGLE | HARWIN |

Light Failure Module.

| Commercial Part No. | Ref. No. | Description | Mfr. |
| --- | --- | --- | --- |
| LM339D | U1'–U8',U15'–U18, | QUADRUPLE DIFFERENTIAL COMPARATOR | TI |
| LM324D | U11'–U14' | QUADRUPLE OPERATIONAL AMPLIFIERS | TI |
| 180-7672 | U10' | SOCKET SMD FOR PLCC44 | RS |
| EPM7032SLC44-10 | U10' | PLD (MAX7000S) | ALTERA |
| $\mu$A7805C | U9' | POSITIVE VOLTAGE REGULATOR + 5VDC | TI |
| AK100/3 | P1 | TERMINAL BLOCK 3 WAY | ELEOTROSPEED |

-continued

Light Failure Module.

| Commercial Part No. | Ref. No. | Description | Mfr. |
|---|---|---|---|
| AK100/16 | P5 | TERMINAL BLOCK 16 WAY | ELEOTROSPEED |
| AK100/2 | P3 | TERMINAL BLOCK 2 WAY | ELEOTROSPEED |
| 471-085 | P2,P4 | CONNECTOR 40 WAY MALE | RS |
| 136-389 | RP1,RP2 | ISOLATED RESISTOR 8 WAY 100 OHMS | RS |
| 109-334 | TP13–TP28 | TRIMMERS MULTITURN 10 K OHMS, 1/4W | FARNELL |
| 169-200 | R70'–R85' | CHIP RESISTOR 100 K OHMS, 1/4W | RS |
| 179-938 | U9' | HEATSINK | FARNELL |
| 109-341 | TP1–TP12 | TRIMMERS MULTITURN 10 K OHMS | FARNELL |
| 176-7956 | R1',R1B,R35', R52',R86–R97' | RESISTOR 10M OHMS 1/4W | RS |
| 472-938 | P6,P7 | PCB HEADER 72 WAY | RS |
| 108-255 | C1' | CAPACITOR ELECTROLYTIC 33 $\mu$F, 25 V | RS |
| 128-237 | C2' | CAPACITOR TANTALUM 10 $\mu$F,35 V | RS |
| 209-748B | CU1–CU16 | CAPACITOR TANTALUM $\mu$F,35 V | RS |
| 126-398 | C4',C8',C8', C10' | CAPACITOR MULTILAYER 0. $\mu$F,63 V | RS |
| 126-382 | C3',C5',C7',C9', C11'–C22' | CAPACITOR MULTILAYER 0.047 $\mu$F, 100 V | RS |
| 169-250 | R2'–R17',R19'–R34' R36–R51', R53'–R68 | CHIP RESISTOR 1 M OHMS 1/4W | RS |

Although preferred embodiments of an adaptive lighting system have been described in detail herein, those skilled in the art will also recognize that various substitutions and modifications may be made to the systems without departing from the scope and spirit of the appended claims.

What is claimed is:

1. An adaptive lighting system for a machine vision apparatus comprising:

an array of plural optical fiber light emitting elements supported for projecting light from one end thereof, respectively, on an article to be viewed, said optical fiber elements being disposed in proximity to plural flash lamps of said system for generating a source of light to be projected through said optical fiber element and on said article;

a camera for recording an image of said article when illuminated by said array;

a light intensity control circuit operably coupled to said array for varying the intensity of light emitted by selected segments of said array to adjust the illumination of said article viewed by said camera;

a processor operably connected to said camera and to said intensity control circuit for adjusting the light intensity emitted by said array to provide an image of said article recorded by said camera; and a flash lamp driver and trigger circuit operably connected between respective ones of said flash lamps and said light intensity control circuit for operating said flash lamps in response to a signal generated by said light intensity control circuit.

2. The system set forth in claim 1 wherein:

said array comprises plural rows of light emitting elements arranged in a generally rectangular pattern about an aperture in said array for projecting an image from said article to said camera.

3. The system set forth in claim 1 wherein:

said processor includes a memory circuit, said memory circuit having data stored therein representing at least one of a predetermined number of images of a predetermined number of articles and values of light intensity emittable by said selected segments of said array.

4. The system set forth in claim 1 including:

a control circuit for generating a flash lamp trigger signal for selectively energizing said flash lamps, respectively, at least one of momentarily and continuously at a predetermined frequency.

5. An adaptive lighting system for a machine vision apparatus for inspecting selected semiconductor packages, said system comprising:

an array of plural light emitting diodes divided into a plurality of segments of at least one light emitting diode per segment and disposed in a pattern for illuminating a semiconductor package for providing an image of said semiconductor package suitable for inspection of said semiconductor package;

a camera disposed with respect to said array for recording an image of said semiconductor package when said semiconductor package is illuminated by said array;

a light intensity control circuit operably coupled to said array for varying the intensity of light emitted by selected segments of said array to provide an image of said semiconductor package having a predetermined resolution;

a processor operably connected to said camera and to said intensity control circuit for adjusting the light intensity emitted by selected segments of said array to provide an image of said package corresponding substantially to said image of predetermined resolution; and said intensity control circuit includes a plurality of digital potentiometers operably connected to respective ones of said segments of said array and operable to receive control signals from said processor for causing predetermined light intensities to be emitted by the light emitting diodes of said segments, respectively, to obtain an image of said package corresponding to said image of predetermined resolution.

6. The system set forth in claim 5 wherein:

said intensity control circuit includes constant current sources interconnected between said potentiometers and said segments, respectively.

7. The system set forth in claim 5 including:

means for switching output signals from said intensity control circuit between selected ones of said segments to enable said camera to capture images of said package having respective different lighting imposed thereon.

8. The system set forth in claim 5 including:

a circuit operable to provider an output signal to cause all segments of said array to illuminate said package substantially simultaneously.

9. An adaptive lighting system for a machine vision apparatus for inspecting selected semiconductor packages, said system comprising:

an array of plural light emitting elements divided into a plurality of segments of at least of one light emitting element per segment and disposed in a pattern for illuminating a semiconductor package to provide an image of said package suitable for inspection of said package;

a camera disposed with respect to said array for recording an image of said package when said package is illuminated by said array;

a light intensity control circuit operably coupled to said array for varying the intensity of light emitted by selected segments of said array to provide an image of said package having a predetermined contrast, said control circuit including plural potentiometers operably connected to respective ones of said segments of said array and operable to receive control signals from a processor for causing predetermined light intensities to be emitted by the light emitting elements of said segments, respectively;

switch means interposed a selected one or more of said potentiometers and said light emitting diodes operably connected to said one or more potentiometers for switching output signals from said one or more potentiometers between selected ones of said segments to enable said camera to capture images of said package having respective different lighting imposed thereon; and a processor operably connected to said camera and said intensity control circuit for adjusting the light intensity emitted by said array to provide images of said package at respective different light intensities imposed thereon.

10. The system set forth in claim 9 wherein:

said switch means comprise analog switches operably connected to respective ones of said potentiometers.

11. An adaptive lighting system for a machine vision apparatus, said system comprising:

an array of plural optical fiber elements divided into a plurality of segments of at least optical fiber element per segment and disposed in a pattern for illuminating an article to provide an image of said article suitable for inspection thereof;

a plurality of flash lamps disposed to transmit light from one end of said optical fiber elements, respectively, to the opposite end for illuminating said article; and a control circuit operably coupled to said flash lamps, respectively, for controlling light generated by said flash lamps and emitted by said optical fiber elements of said array to provide an image of said article.

12. The system set forth in claim 11 including:

a flash lamp driver and trigger circuit operably connected between respective ones of said flash lamps and said control circuit for operating said flash lamps in response to a signal generated by said control circuit.

13. The system set forth in claim 12 including:

a control circuit for generating a flash lamp trigger signal for selectively energizing said flash lamps, respectively, at least one of momentarily and continuously at a predetermined frequency.

14. A method for illuminating a semiconductor package for viewing by a machine vision apparatus wherein said machine vision apparatus includes a lighting array comprising a plurality of light emitting elements, a camera for recording an image of said package when illuminated by said array and a processor including a circuit for recording an image captured by said camera, a memory, a processor circuit and a lighting intensity control circuit for controlling the intensity of light emitted by at least selected ones of said light emitting elements to adjust the illumination of said package, said method comprising the steps of:

(a) retrieving a set of light intensity values for selected ones of said lighting elements from a file in said processor corresponding to selected physical characteristics of said package;

(b) illuminating first and second sets of light emitting elements of said array at respective predetermined intensities;

(c) capturing an image of said package with said array illuminated at said predetermined intensities of said first and second sets of light emitting elements;

(d) illuminating said first set of light emitting elements at the intensity settings of said second set of light emitting elements in step (b) and illuminating said second set of light emitting elements at the intensity settings of said first set of light emitting elements in step (b);

(e) capturing an image of said package with said array illuminated as set forth in step (d); and (f) comparing the images captured in steps (c) and (e).

15. A method for illuminating a semiconductor package for viewing by a machine vision apparatus wherein said machine vision apparatus includes a lighting array comprising a plurality of light emitting elements arranged in a predetermined pattern, said light emitting elements being divided into plural segments of said pattern, a camera for recording an image of said package when illuminated by said array in accordance with a preselected intensity of light emitted by selected ones of said segments and a processor including a circuit for recording an image captured by said camera, a memory, a processor circuit and a lighting intensity control circuit for controlling the intensity of light emitted by said selected ones of said light emitting elements, said method comprising the steps of:

(a) identifying a package viewed by said camera by physical characteristics of said package;

(b) illuminating said package with light emitting elements of a preselected number of segments of said lighting array;

(c) capturing an image of said package with said camera while illuminated with said preselected number of segments;

(d) from time to time illuminating said package with a number of segments of said lighting array greater than the number of segments illuminated in step (b); and (e) capturing an image of said package while illuminated with said greater number of segments.

16. An adaptive lighting system for a machine vision apparatus comprising:

an array of plural light emitting elements supported for projecting light on an article to be viewed;

a camera for recording an image of said article when illuminated by said array;

a light intensity control circuit operably coupled to said array including a plurality of potentiometers operably connected to respective selected segments of said array for controlling the intensity of light emitted by the light emitting elements of said segments, respectively, to adjust the illumination of said article viewed by said camera to obtain a predetermined image of said article; and a processor operably connected to said camera and to said intensity control circuit for adjusting the light intensity emitted by said array to provide said image of said article recorded by said camera.

17. The system set forth in claim 16 wherein:

said array of light emitting elements comprises an array of plural light emitting diodes (LEDs).

18. The system set forth in claim 17 wherein:

said light emitting elements are disposed substantially uniformly about said article.

19. The system set forth in claim 17 including:

a circuit including circuit elements operable to provide an output signal to cause all segments of said array to illuminate said article momentarily and substantially simultaneously.

20. The system set forth in claim 16 wherein:

said array comprises plural rings of light emitting elements arranged concentrically on a support structure about an aperture in said support structure.

21. The system set forth in claim 16 wherein:

said potentiometers comprise digital potentiometers operable to receive control signals from said processor for causing predetermined light intensities to be emitted by said light emitting elements of said segments, respectively.

22. The system set forth in claim 16 wherein:

said control circuit includes constant current sources interconnected between said potentiometers and said segments, respectively.

23. The system set forth in claim 22 wherein:

said constant current sources comprise, respectively, operational amplifiers in circuit with power MOSFETs and interposed said potentiometers and the lighting elements of said segments.

24. The system set forth in claim 16 including:

switch means for switching output signals from said intensity control circuit between selected ones of said segments.

25. An adaptive lighting system for a machine vision apparatus comprising:

an array of plural light emitting diodes (LEDs) supported for projecting light on an article to be viewed;

a camera for recording an image of said article when illuminated by said array;

a light intensity control circuit operably coupled to said array for varying the intensity of light emitted by selected segments of said array to adjust the illumination of said article viewed by said camera;

a circuit including a potentiometer connected to a monostable multi-vibrator timing circuit operable to provide an output signal to cause all segments of said array to illuminate said article momentarily and substantially simultaneously; and a processor operably connected to said camera and to said intensity control circuit for adjusting the light intensity emitted by said array to provide an image of said article recorded by said camera.

26. An adaptive lighting system for a machine vision apparatus comprising:

an array of plural light emitting elements supported for projecting light on an article to be viewed;

a camera for recording an image of said article when illuminated by said array;

a light intensity control circuit operably coupled to said array for varying the intensity of light emitted by selected segments of said array to adjust the illumination of said article viewed by said camera;

a processor operably connected to said camera and to said intensity control circuit for adjusting the light intensity emitted by said array to provide an image of said article recorded by said camera; and a light failure module operably connected to said system and operable to provide a signal indicating the failure of one or more light emitting elements of said array.

27. The system set forth in claim 26 wherein:

said light failure module includes voltage comparator means for detecting an open circuit or reverse connection of said one or more light emitting elements of said array.

28. The system set forth in claim 27 wherein:

said light failure modul includes voltage comparator means for comparing a reference voltage with a voltage at a power MOSFET operably coupled to each of said segments of light emitting elements.

* * * * *